United States Patent [19]
Dack et al.

[11] Patent Number: 6,040,309
[45] Date of Patent: Mar. 21, 2000

[54] BENZOTHIOPHENE DERIVATIVES USEFUL IN THERAPY

[75] Inventors: Kevin Neil Dack, Sandwich, United Kingdom; Roger Peter Dickinson, New York, N.Y.

[73] Assignee: Pfizer, Inc., New York, N.Y.

[21] Appl. No.: 09/204,789

[22] Filed: Dec. 3, 1998

[30] Foreign Application Priority Data

Dec. 8, 1997 [GB] United Kingdom ............ 9725953

[51] Int. Cl.[7] .................. C07D 333/64; A61K 31/38
[52] U.S. Cl. ................ 514/253; 514/254; 514/255; 514/269; 514/337; 514/397; 514/443; 544/238; 544/333; 544/376; 546/118; 546/281.1; 548/311.4; 549/52; 549/54
[58] Field of Search .................. 514/253, 254, 514/255, 269, 337, 397, 443; 544/238, 333, 376; 546/118, 281.1; 548/311.4; 549/52, 54

[56] References Cited

U.S. PATENT DOCUMENTS

| | | | |
|---|---|---|---|
| 5,440,046 | 8/1995 | Wagner et al. .............. | 548/322.5 |
| 5,482,960 | 1/1996 | Berryman, et al. ............ | 514/414 |
| 5,703,116 | 12/1997 | Gaeta et al. ................ | 514/443 |

FOREIGN PATENT DOCUMENTS

| | | |
|---|---|---|
| 0050957 | 5/1982 | European Pat. Off. . |
| 2118552 | 11/1983 | United Kingdom . |

OTHER PUBLICATIONS

Connor et al., *Novel Benzothiophene, Benzofuran, and Naphthalenecarboxamidotetrazoles as Potential Atniallergy Agents*, J. Med. Chem., 35 (5), pp. 958–965, 1992.

Amy M. Bunker, et al., *1–Benzyl–3–Thioaryl–2–Carboxyindoles as Potent Non-–peptide Endothelin Antagonists*, vol. 6, No. 12, Bioorganic & Medicinal Chemistry Letters, pp. 1367–1370, 1996.

Peter E. Cross, et al., *Selective Thromboxane Synthetase Inhibitors. 3. 1H–Imidazol–1–yl–Substituted Benzo[b]furan–Benzo[b]thiophene–, and Indole–2– and –3–carboxylic Acids*, vol. 29, No. 9, Journal of Medicinal Chemistry, pp. 1637–1643, 1986.

*Primary Examiner*—Mukund J. Shah
*Assistant Examiner*—Deepak R. Rao
*Attorney, Agent, or Firm*—Peter C. Richardson; Gregg C. Benson; Todd M. Crissey

[57] ABSTRACT

Compounds of formula I,

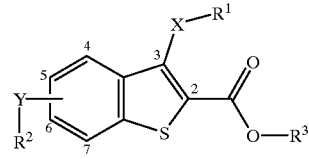

I wherein

X represents O or $S(O)_m$;

$R^1$ and $R^2$ independently represent phenyl, naphthyl or heteroaryl; each of which is optionally fused and optionally substituted;

Y represents a bond, O, $(CH_2)_n$, $O(CH_2)_n$, $(CH_2)_nO$, or $CH(C_{1-6}\text{ alkyl})O$;

$R^3$ represents H or $C_{1-6}$ alkyl;

m represents 0, 1, or 2; and n represents 1, or 2;

and pharmaceutically acceptable salts thereof, are useful in therapy, in particular in the treatment of restenosis, renal failure and pulmonary hypertension.

10 Claims, No Drawings

BENZOTHIOPHENE DERIVATIVES USEFUL IN THERAPY

This application claims priority from U.K. application serial no. 9725953.5 which was filed on Dec. 8, 1997.

This invention relates to benzo[b]thiophene-2-carboxylic acid derivatives useful in the treatment of a variety of diseases including restenosis, renal failure and pulmonary hypertension, and to pharmaceutical formulations containing such compounds.

Certain benzo[b]thiophene-2-carboxylic acids have been reported to have the ability to antagonise the effect of endothelin at the $ET_A$ receptor while having a weaker effect at the $ET_B$ receptor [Bioorg & Med Chem Letts 12, p1367–1370, (1996)]. In particular, 5-benzyloxy-3-isopropoxybenzo[b]thiophene-2-carboxylic acid and 3-[(3-methoxyphenyl)sulfanyl]benzo[b]thiophene-2-carboxylic acid have an $IC_{50}$ against the rabbit $ET_A$ receptor of 6 and 5.9 μM respectively. The former compound has an $IC_{50}$ of 8.8 μM against the human $ET_A$ receptor. It was reported that the I-position plays a role in receptor binding, and compounds of much greater affinity were obtained by replacement of the sulfur atom by N-(substituted benzyl) to give indole analogues (U.S. Pat. No. 5,482,960). Furthermore, structure-activity studies in the resulting indole series indicated that methoxy substitution at the indole 5- and 6-positions was necessary for optimal potency. Replacement of the 6-methoxy with 6-benzyloxy was highly detrimental giving a ~1,000-fold reduction in potency (cf examples 21 and 22 in the Bioorg & Med Chem Letts reference).

Benzo[b]thiophene-2-carboxylic acid derivatives have also been indicated as inhibitors of thromboxane synthase (see EP 50957 and GB 2,118,552).

According to the present invention, there is provided a compound of formula I,

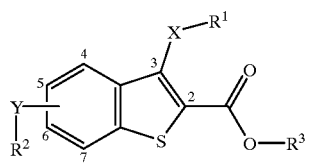

I wherein
  X represents O or $S(O)_m$;
  $R^1$ and $R^2$ independently represent phenyl, naphthyl or heteroaryl containing 1, 2 or 3 heteroatoms independently selected from N, S and O; the ring being optionally fused to a saturated or unsaturated heterocyclic ring containing 1, 2 or 3 heteroatoms independently selected from N, S and O; the ring system as a whole being optionally substituted by one or more groups selected from OH, halogen, CN, $NH_2$, $(CH_3SO_2)HN$, $(CH_3SO_2)_2N$, $C_{1-6}$ alkyl (optionally substituted by OH or $CH_3CO_2$) and $C_{1-6}$ alkoxy;
  Y represents a bond, O, $(CH_2)_n$, $O(CH_2)_n$, $(CH_2)_nO$, or $CH(C_{1-6}$ alkyl)O;
  $R^3$ represents H or $C_{1-6}$ alkyl;
  m represents 0, 1, or 2; and
  n represents 1, or 2;
  provided that:
    (i) when $R^2$ is linked to Y via a nitrogen atom, then Y does not represent O, $O(CH_2)_n$ or $CH_2O$; and
    (ii) when $R^3$ represents H, then neither $R^1$ nor $R^2$ is substituted by $(CH_3SO_2)_2N$;

or a pharmaceutically acceptable salt thereof (referred to together herein as "the compounds of the invention").

The compounds excluded by the provisos are not sufficiently stable to be useful as drugs.

Groups that Y represents are written starting with the atom most remote from the benzo ring: for example "$O(CH_2)_n$" has $R^2$ attached to the oxygen atom and the benzo ring attached to a carbon atom.

Pharmaceutically acceptable salts include alkali metal salts (for example sodium salts) of any acidic groups that may be present, and acid addition salts (for example ammonium salts) of any basic groups that may be present.

"Halogen" includes fluorine, chlorine, bromine and iodine.

Alkyl groups which $R^{1-3}$ and Y represent or comprise may be straight chain, branched or cyclic.

Specific heteroaryl groups that $R^1$ and $R^2$ may represent or comprise include pyridyl, pyrimidinyl, imidazolyl, thienyl, triazolyl, pyrazinyl, pyridazinyl and thiazolyl.

Preferred groups of compounds include those in which:
  (a) X represents SO or S;
  (b) $R^1$ represents phenyl or substituted phenyl, for example phenyl substituted by methoxy;
  (c) $R^2$ represents 3-pyridyl, 5-pyrimidinyl, 1-imidazolyl, imidazo[4,5-c]pyridin-3-yl or 3-thienyl;
  (d) Y represents $CH_2$, $CH_2O$ or $OCH_2$;
  (e) Y is attached to the 6-position of the benzothiophene ring;
  (f) $R^3$ represents H; and
  (g) a heteroatom in $R^2$ is separated from the benzothiophene ring by 4 atoms.

According to the invention, there is also provided a process for the production of a compound of formula I, as defined above, or a pharmaceutically acceptable salt thereof, which comprises:
  (a) hydrolysis of a compound of formula I in which $R^3$ represents $C_{1-6}$ alkyl, to produce a corresponding compound of formula I in which $R^3$ represents H;
  (b) oxidation of a compound of formula I in which X represents S and $R^3$ represents $C_{1-6}$ alkyl, to produce a corresponding compound of formula I in which X represents SO or $SO_2$;
  (c) when X represents S or O, reaction of a compound of formula II,

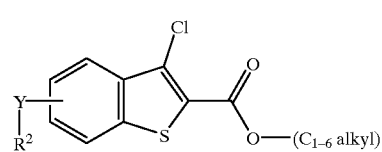

II wherein Y and $R^2$ are as defined above, with a compound of formula III, $HX^aR^1$  III wherein $R^1$ is as defined above and $X^a$ represents S or O, in the presence of a base;
  (d) when Y represents $(CH_2)_nO$ or $CH(C_{1-6}$ alkyl)O, reaction of a compound of formula V,

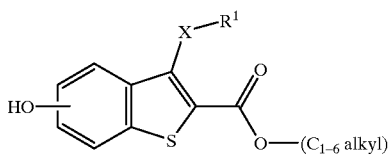

wherein X and R¹ are as defined above, with a compound of formula Va,

R²Y^a Z    Va wherein R² is as defined above, Y^a represents $(CH_2)_n$ or $CH(C_{1-6}$ alkyl), and Z represents a leaving group or OH;

(e) when Y represents $O(CH_2)_n$, reaction of a compound of formula VII,

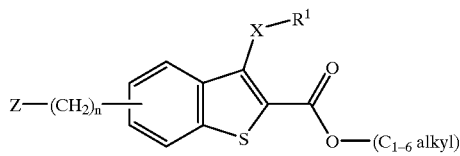

wherein X, R¹ and n are as defined above, and Z is a leaving group, with a compound of formula VIIa, R²OH    VIIa wherein R² is as defined above, in the presence of a base;

(f) when Y represents $(CH_2)_n$ and R² represents N-linked heteroaryl, reaction of a compound of formula VII, as defined above, with a compound of formula VIIb, R^{2a}H    VIIb wherein $R^{2a}$ represents an N-containing heteroaromatic compound with a hydrogen atom attached to the N, in the presence of a base;
and where desired or necessary converting the resulting compound of formula I into a pharmaceutically acceptable salt or vice versa.

In process (a), the hydrolysis may be carried out in a solvent which does not adversely affect the reaction (for example 1,4-dioxane or methanol) in the presence of a base (such as sodium hydroxide), at an elevated temperature.

In process (b), suitable oxidizing agents include hydrogen peroxide. The oxidation may be carried out in a solvent which does not adversely affect the reaction (for example acetic acid), at an elevated temperature. When producing a compound in which X represents SO, controlled oxidation using a stoichiometric amount of hydrogen peroxide, or sodium metaperiodate in aqueous methanol or acetic acid at a temperature ranging from ambient to reflux, is preferred.

In process (c), when $X^a$ represents S, suitable bases include 1,8-diazabicyclo[5.4.0]undec-7-ene (DBU). The reaction may be carried out in a solvent which does not adversely affect the reaction (for example dimethylformamide), at a temperature of 20–100° C. When $X^a$ represents O, similar conditions may be used, except that sodium hydride is a suitable base.

In process (d), suitable leaving groups that Z may represent include halogen (such as chloro), methanesulfonate and toluenesulfonate. The reaction may be carried out in a solvent which does not adversely affect the reaction (for example dimethylformamide), at ambient temperature. Suitable bases include potassium carbonate. Alternatively, when Z represents OH, a Mitsunobu reaction may be performed using a phosphine and a dialkyldiazocarboxylate.

A process analogous to process (d) may also be used at an earlier stage in the synthesis on a compound analogous to compounds of formula V but in which XR¹ is replaced with Cl, to give a compound of formula II.

In process (e), suitable leaving groups that Z may represent include halogen (such as chloro), methanesulfonate and toluenesulfonate. The reaction may be carried out in a solvent which does not adversely affect the reaction (for example dimethylformamide), at ambient temperature. Suitable bases include sodium hydride and potassium carbonate.

A process analogous to process (d) may also be used at an earlier stage in the synthesis on a compound analogous to compounds of formula VII but in which XR¹ is replaced with Cl, to give a compound of formula II.

In process (f), suitable leaving groups that Z may represent include halogen (such as bromo). The reaction may be carried out in a solvent which does not adversely affect the reaction (for example dimethylformamide), around 0° C. Suitable bases include sodium hydride and potassium carbonate.

Compounds of formula II may be prepared from a propenoic acid of formula IV,

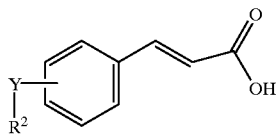

wherein R² and Y are as defined above, by reaction with thionyl chloride followed by treatment of the resulting acid chloride with an alcohol to give the desired ester. The reaction with thionyl chloride is described in WO 95/15323 and by A J Krubsack and T Higa in Journal of Organic Chemistry 1976, 41(21), 3399–3403.

Compounds of formula V may be obtained from corresponding compounds of formula I in which R²Y represents benzyloxy, by hydrogenation over a palladium catalyst in a solvent such as ethanol, or by treatment with trifluoroacetic acid in the precence of a carbonium scavenger such as thioanisole at ambient temperature.

Compounds of formula VII in which Z is a leaving group may be prepared from corresponding compounds of formula VII in which Z is OH by standard methods; for example, reaction with methanesulfonyl chloride in dichloromethane in the presence of a base such as triethylamine to give a compound in which Z is methanesulfonate. Alternatively, compounds of formula VII in which Z is Br or Cl and n is 1 may be prepared from corresponding compounds of formula IX,

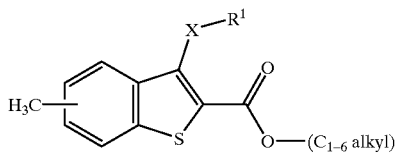

in which X and $R^1$ are as defined above, by reaction with N-bromosuccinimide or N-chlorosuccinimide in an inert solvent such as $CCl_4$.

Compounds of formula VII in which Z is OH and n is 2 may be prepared analogously to compounds of formula I, for example by starting with a compound analogous to a compound of formula IV in which $R^2Y$ is replaced with benzyl-$OCH_2CH_2$, and then deprotecting the resulting compound by hydrogenolysis.

Compounds of formula VII in which Z is OH may be prepared from corresponding compounds of formula VII in which Z is Br or Cl, by treatment with sodium acetate to give compounds substituted by $CH_3CO_2$, followed by ester cleavage using potassium carbonate in ethanol.

Compounds of formula IX may be prepared analogously to compounds of formula I, for example starting with a compound analogous to a compound of formula IV but in which $R^2Y$ is replaced with an appropriate alkyl group.

The intermediate compounds of formulae V and VII, as defined above, form a further aspect of the invention.

Compounds of formulae III, IV, Va, VIIa and VIIb are either known or are available using known techniques.

The compounds of the invention may be separated and purified by conventional methods.

It will be apparent to those skilled in the art that sensitive functional groups may need to be protected and deprotected during synthesis of a compound of formula I. This may be achieved by conventional techniques, for example as described in 'Protective Groups in Organic Synthesis' by T W Greene and P G M Wuts, John Wiley and Sons Inc, 1991.

The compounds of formula I may possess one or more chiral centres and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of formula I.

The compounds of formula I may exist in one or more tautomeric forms. All tautomers and mixtures thereof are included in the scope of the present invention.

The compounds of formula I are useful because they have pharmacological activity in animals, including humans. More particularly, they are useful in the treatment of restenosis, renal failure, pulmonary hypertension, benign prostatic hypertrophy, male erectile dysfunction, congestive heart failure, stroke, angina, atherosclerosis, cerebral and cardiac ischaemia or cyclosporin induced nephrotoxicity. The treatment of restenosis, renal failure, pulmonary hypertension and male erectile dysfunction are of particular interest. The compounds of formula I may be administered alone or as part of a combination therapy. Treatment of companion animals such as dogs and cats is also contemplated.

Thus, according to a further aspect of the invention, there is provided a compound of formula I, as defined above, or a pharmaceutically acceptable salt thereof, for use as a pharmaceutical.

There is further provided a pharmaceutical formulation comprising a compound of formula I, as defined above, or a pharmaceutically acceptable salt thereof, and a pharmaceutically acceptable adjuvant, diluent or carrier.

The invention also provides the use of a compound of formula I, as defined above, or a pharmaceutically acceptable salt thereof, in the manufacture of a medicament for the treatment of restenosis, renal failure, pulmonary hypertension, benign prostatic hypertrophy, male erectile dysfunction, congestive heart failure, stroke, angina, atherosclerosis, cerebral and cardiac ischaemia or cyclosporin induced nephrotoxicity. The invention also provides a method of treatment of these diseases, which comprises administering a therapeutically effective amount of a compound of formula I, as defined above, or a pharmaceutically acceptable salt thereof, to a patient in need of such treatment.

Without being limited by theory, the compounds of formula I are believed to be endothelin receptor antagonists. Endothelin (ET) is a potent vasoconstrictor synthesised and released by endothelial cells. There are three distinct isoforms of ET: ET-1, ET-2 and ET-3, all being 21-amino acid peptides and herein the term 'endothelin' refers to any or all of the isoforms. Two receptor subtypes, $ET_A$ and $ET_B$ have been pharmacologically defined (see for example H. Arai et al, Nature, 348, 730, 1990) and further subtypes have recently been reported. Stimulation of $ET_A$ promotes vasoconstriction and stimulation of $ET_B$ receptors causes either vasodilation or vasoconstriction.

The effects of endothelin are often long-lasting and, as the endothelins are widely distributed in mammalian tissues, a wide range of biological responses has been observed in both vascular and non-vascular tissue. The main effects of endothelin are observed in the cardiovascular system, particularly in the coronary, renal, cerebral and mesenteric circulation.

Increased circulating levels of endothelin have been observed in patients who have undergone percutaneous transluminal coronary angioplasty (PTCA) (A. Tahara et al, Metab. Clin. Exp. 40, 1235, 1991) and ET-1 has been found to potentiate neointimal formation in rats after balloon angioplasty (S. Douglas et al, J.Cardiovasc.Pharm., 22 (Suppl 8), 371, 1993). The same workers have found that an endothelin antagonist, SB-209670, causes a 50% reduction in neointimal formation relative to control animals (S. Douglas et al, Circ Res, 75, 1994). Antagonists of the endothelin receptor may thus be useful in preventing restenosis post PTCA.

Endothelin-1 is produced in the human prostate gland and endothelin receptors have been identified in this tissue. Since endothelin is a contractile and proliferative agent endothelin antagonists could be useful in the treatment of benign prostate hypertrophy.

There is widespread localisation of endothelin and its receptors in the central nervous system and cerebrovascular system (R. K. Nikolov et al, Drugs of Today, 28(5), 303, 1992) with ET being implicated in cerebral vasospasm, cerebral infarcts and neuronal death. Elevated levels of endothelin have also been observed in patients with:

Chronic renal failure (F. Stockenhuber et al, Clin Sci (Lond.), 82, 255, 1992)

Ischaemic Heart Disease (M. Yasuda, Am. Heart J., 119, 801, 1990)

Stable or unstable angina (J. T. Stewart, Br. Heart J. 66, 7 1991)

Pulmonary Hypertension (D. J. Stewart et al, *Ann. Internal Medicine*, 114, 464, 1991)

Congestive heart failure (R. J. Rodeheffer et al, *Am.J.Hypertension*, 4, 9A, 1991)

Preeclampsia (B. A. Clark et al, *Am.J.Obstet.Gynecol.*, 166, 962, 1992)

Diabetes (A. Collier et al, *Diabetes Care*, 15 (8), 1038, 1992)

Crohn's disease (S. H. Murch et al, *Lancet*, 339, 381, 1992)

Atherosclerosis (A. Lerman et al, *New Eng. J. Med.*, 325, 997, 1991)

In every case the disease state associated with the physiologically elevated levels of endothelin is potentially treatable with an endothelin receptor antagonist and hence a compound of formula I.

Compounds that selectively antagonise the $ET_A$ receptor rather than the $ET_B$ receptor are preferred.

The biological activity of the compounds of formula I may be demonstrated in Tests A–C below:

A. Binding Assay

Competition between test compounds and $^{125}$I-ET-1 binding to human endothelin receptors is determined as follows.

Binding to $ET_A$ Receptors

25 μl of a 30 pM solution of [$^{125}$I]Tyr$^{13}$ ET-1 (specific activity 2,200 Ci/mM) is mixed with 25 μl samples of test compound (final concentrations in the range 0.1 nM–50,000 nM). 200 μl of a solution containing cloned human $ET_A$ receptor (0.75 pmoles receptor protein/ml), 50 mM Tris, 0.5 mM $CaCl_2$, 0.1% human serum albumen, 0.1% bacitracin, 0.05% Tween 20, pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radioactivity, and the $IC_{50}$ (the concentration of test compound at which 50% of the radiolabelled compound is unbound) determined for the concentration range tested.

Binding to $ET_B$ Receptors

25 μl of a 30 pM solution of [$^{125}$I]Tyr$^{13}$ ET-1 (specific activity 2,200 Ci/M) is mixed with 25 μl samples of test compound (final concentration 0.1 nM–50,000 nM). 200 μl of a solution containing cloned human $ET_B$ receptor (0.25 pmoles receptor protein/ml), 50 mM Tris, 0.5 mM $CaCl_2$, 0.1% human serum albumen, 0.1% bacitracin, 0.05% Tween 20, pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radio-activity, and the $IC_{50}$ (the concentration of test compound at which 50% of the radio-labelled compound is unbound) determined for the concentration range tested.

B. In Vitro Vascular Smooth Muscle Activity

Rat Aorta

Rat aortae are cleaned of connective tissue and fat and cut into helical strips approx 4 mm in width. The endothelium is removed by dragging the luminal surface of the tissue gently across filter paper moistened with Krebs solution of composition (mM) NaCl 130, KCl 5.6, $NaHCO_3$ 25, Glucose 11.1, $NaH_2PO_4$ 0.6, $CaCl_2$ 2.16, $MgCl_2$ 0.5, gassed with 95% $O_2$/5% $CO_2$. The strips are mounted in isolated organ baths in Krebs solution under a resting tension of 1 gram. Organ bath solutions are maintained at 37° C. and continuously aerated with 95% $O_2$/5% $CO_2$. Tensions are measured with Maywood Industries isometric force transducers and displayed on Gould TA4000 recorders. After equilibration in the organ bath for 1 hour, tissues are contracted by the addition of KCl to a final concentration of 60 mM. The KCl is removed by replacing the Krebs solution, with two further washes with Krebs solution. To determine the potency of an $ET_A$ receptor antagonist, two tissues are cumulatively dosed with ET-1 (0.1 nM–1 μM); other tissues are dosed with ET-1 (0.1 nM–1 μM) in duplicate, beginning 30 minutes after the inclusion in the organ bath medium of the test compound. Sufficient tissues are used per experiment to generate dose-response curves to ET-1 in the absence and the presence of at least 3 concentrations of antagonist. Data are expressed as the mean±s.e.m. Dissociation constants ($k_b$) of competitive antagonists are calculated by the method of Arunlakshana and Schild.

Rabbit Pulmonary Artery

Isolated rabbit pulmonary arteries are cleaned of connective tissue and fat and cut into rings approx 4 mm in width. The endothelium is removed by inserting a fibrous instrument moistened with Krebs solution of composition (mM) NaCl 130, KCl 5.6, $NaHCO_3$ 25, Glucose 11.1, $NaH_2PO_4$ 0.6, $CaCl_2$ 2.16, $MgCl_2$ 0.5, gassed with 95% $O_2$/5% $CO_2$. The rings are mounted in isolated organ baths in Krebs solution under a resting tension of 1 gram. Organ bath solutions are maintained at 37° C. and continuously aerated with 95% $O_2$/5% $CO_2$. Tensions are measured with Maywood Industries isometric force transducers and displayed on Gould TA4000 recorders. After equilibration in the organ bath for 1 hour, tissues are contracted by the addition of KCl to a final concentration of 60 mM. The KCl is removed by replacing the Krebs solution, with two further washes with Krebs solution. To determine the potency of an $ET_B$ receptor antagonist, two tissues are cumulatively treated with BQ-3020 (0.1 nM–1 μM); other tissues are treated with BQ-3020 (0.1 nM–1 μM) in duplicate, beginning 30 minutes after the inclusion in the organ bath medium of the test compound. Sufficient tissues are used per experiment to generate dose-response curves to BQ-3020 in the absence and the presence of at least 3 concentrations of antagonist. Data are expressed as the mean±s.e.m. Dissociation constants ($k_b$) of competitive antagonists are calculated by the method of Arunlakshana and Schild.

C. In Vivo Blockade of Endothelin-induced Blood Pressure Elevation

In anaesthetised, ganglion-blocked and artificially respired rats, the left common carotid artery and the right jugular vein are cannulated for the measurement of arterial blood pressure and the administration of compound respectively. Rats are treated with the $ET_B$ antagonist BQ-788 (0.25 mg/kg i.v.). Beginning 10 minutes after administering BQ-788, the hypertensive response to ET-1 (1 μg/kg i.v.) is determined. When the blood pressure has returned to baseline, the test compound is administered (0.1–20 mg/kg i.v.) and after 10 minutes the ET-1 challenge is repeated. Increasing concentrations of the test compound are administered, followed 10 minutes after each administration by a further ET-1 challenge. An $IC_{50}$ is determined based upon inhibition of ET-1 induced pressor response upon cumulative dosing with compound.

Duration of blockade is determined in anaesthetised, ganglion-blocked and artificially respired rats, in which the left common carotid artery and the right jugular vein are cannulated for the measurement of arterial blood pressure and the administration of compound respectively. Rats are treated with the $ET_B$ antagonist BQ-788 (0.25 mg/kg i.v.). Beginning 10 minutes after administering BQ-788, the hypertensive response to ET-1 (1 μg/kg i.v.) is determined.

When the blood pressure has returned to baseline, the test compound is administered (10 mg/kg i.v.). Further administrations of ET-1 are made 5, 20 and 60 minutes after dosing the test compound. In separate animals, prepared similarly, an ET-1 challenge is made 2 or 4 hours after dosing with the test compound, in these animals BQ-788 is dosed 10 minutes before the ET-1 challenge. For later time points, rats are dosed with the test compound (10 mg/kg) i.v. via a tail vein or p.o., they are then anaesthetised and prepared for blood pressure measurement as above. In these rats, ET-1 (1 µg/kg i.v.) was administered 6 or 8 hours after the test compound.

For human use the compounds of formula I can be administered alone but will generally be administered in admixture with a pharmaceutical carrier selected with regard to the intended route of administration and standard pharmaceutical practice. For example they can be administered orally in the form of tablets containing such excipients as starch or lactose or in capsules or ovules either alone or in admixture with excipients or in the form of elixirs, solutions or suspensions containing the compound or salt in a liquid carrier, for example a vegetable oil, glycerine or water with a flavouring or colouring agent. They can be injected parenterally, for example intravenously, intramuscularly or subcutaneously. For parental administration, they are best used as sterile aqueous solutions which may contain other substances, for example, enough glucose or salts to make the solution isotonic with blood. For parenteral administration the compound or salt may also be administered as a solution or suspension in a suitable oil, for example polyethylene glycol, lecithin or sesame oil.

Compounds of formula I may also be administered through inhalation of a solution, suspension or emulsion that may be administered as a dry powder or in the form of an aerosol using a conventional propellant such as dichlorodifluoromethane.

For oral or parenteral administration to human patients the daily dosage levels of compounds of formula I will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. The above dosages are, of course only exemplary of the average case and there may be instances where higher or lower doses are merited, and such are within the scope of the invention.

Alternatively the compounds of formula I can be administered in the form of a suppository or pessary, or they may be applied topically in the form of a lotion, solution, cream, ointment or dusting powder or in the form of a medicated plaster, patch or membrane. For example they may be incorporated in a cream containing an aqueous emulsion of polyethylene glycols or liquid paraffin. The compounds may also be administered intranasally.

The invention is illustrated by the following Preparations and Examples, in which the following abbreviations may be used:

| | |
|---|---|
| LRMS | low resolution mass spectroscopy |
| NMR | nuclear magnetic resonance |
| nOe | nuclear Overhauser effect |

Preparation 1

(E)-3-[4-(3-Pyridylmethoxy)phenyl]-2-propenoic Acid

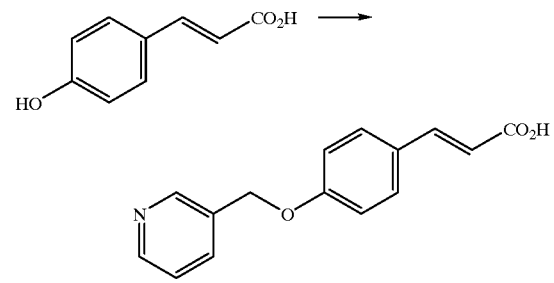

An aqueous solution of 2M NaOH (165 ml) was added to a solution of (E)-3-[4-hydroxyphenyl]-2-propenoic acid (16.4 g, 100 mmol) in ethanol (100 ml). The mixture was stirred for 10 minutes, and then 3-(chloromethyl)-pyridine hydrochloride (19.7 g, 120 mmol) was added in portions. The mixture was stirred for 20 hours, and the solvents were evaporated under reduced pressure. Water was added and the suspension heated to give a solution. To this solution was added acetic acid, and the resultant precipitate was filtered and recrystallised from methanol to give the title compound as a colourless solid (15.6 g).

m.p. 228–230° C.

LRMS (Thermospray): 256.3 (MH$^+$)

$^1$H NMR (300 MHz, DMSO-d$_6$): δ=5.20 (s, 2H), 6.38 (d, 1H), 7.06 (d, 2H), 7.43 (m, 1H), 7.53 (d, 1H), 7.65 (d, 2H), 7.88 (d, 1H), 8.55 (d, 1H), 8.68 (s, 1H), 12.30 (brs, 1H).

Analysis: Found: C, 70.25; H, 5.10; N, 5.43. $C_{15}H_{13}NO_3$ Requires: C, 70.57; H, 5.13; N, 5.49.

Preparation 2

(E)-3-[3-(3-Pyridylmethoxy)phenyl]-2-propenoic Acid

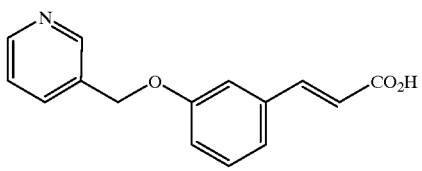

This was prepared by the same procedure as described for Preparation 1, using (E)-3-[3-hydroxyphenyl]-2-propenoic acid.

m.p. 169–171° C.

LRMS (Thermospray): 256.2 (MH$^+$)

$^1$H NMR (300 MHz, DMSO-d$_6$): δ=5.20 (s, 2H), 6.58 (d, 1H), 7.06 (d, 1H), 7.23–7.47 (m, 4H), 7.55 (d, 1H), 7.88 (d, 1H), 8.55 (d, 1H), 8.70 (s, 1H), 12.50 (brs, 1H).

Analysis: Found: C, 70.05; H, 5.08; N, 5.47. $C_{15}H_{13}NO_3$ Requires: C, 70.57; H, 5.13; N, 5.49.

Preparation 3

Methyl 3-chloro-6-(3-pyridylmethoxy)benzo[b]thiophene-2-carboxylate

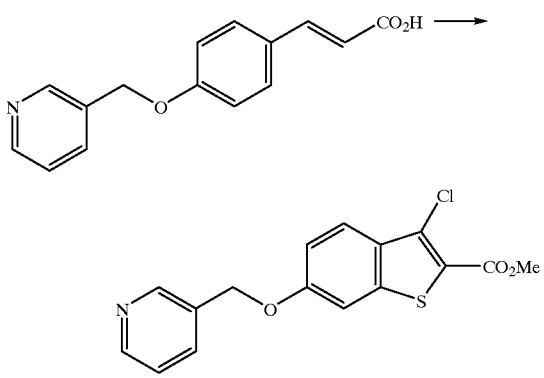

Thionyl chloride (0.72 ml, 10 mmol) was added dropwise to a stirred suspension of (E)-3-[4-(3-Pyridylmethoxy)phenyl]-2-propenoic acid (Preparation 1, 510 mg, 2 mmol) in chlorobenzene (3 ml). The mixture was stirred at ambient temperature for 15 minutes, and then heated at reflux for 3 hours. The reaction mixture was cooled and dimethylformamide (0.15 ml, 2 mmol), and an additional portion of thionyl chloride (0–29 ml, 4 mmol), were added. The mixture was heated at reflux for a further 3 hours before being cooled and poured into methanol (20 ml). The mixture was heated to reflux for 10 minutes, and after cooling, the solvents were removed under reduced pressure. The residue was partitioned between ethyl acetate and aqueous sodium bicarbonate solution, and the organic layer separated, dried (magnesium sulfate) and evaporated under vacuo. The residue was flash chromatographed on silica gel using diethyl ether as eluant, and the product crystallised from diethyl ether and hexane to give the title compound as a colourless solid (310 mg).

m.p. 148–150° C.

LRMS (Thermospray): 334.3 (MH$^+$)

$^1$H NMR (300 MHz, CDCl$_3$): δ=3.95 (s, 3H), 5.18 (s, 2H), 7.19 (d, 1H), 7.30–7.38 (m, 2H), 7.79 (d, 1H), 7.88 (d, 1H), 8.61 (d, 1H), 8.73 (s, 1H).

Analysis: Found: C, 57.45; H, 3.53; N, 4.14. $C_{16}H_{12}ClNO_3S$ Requires: C, 57.57; H, 3.62; N, 4.20.

Preparations 4–9 were prepared similarly using a 3-[(substituted)phenyl]-2-propenoic acids as described above, or 3-[(substituted)phenyl]-2-propenoic acids from commercial or literature sources. The ethyl esters are obtained by substituting ethanol for methanol.

Preparation 4

Ethyl 3-chloro-6-(3-pyridylmethoxy)benzo[b]thiophene-2-carboxylate

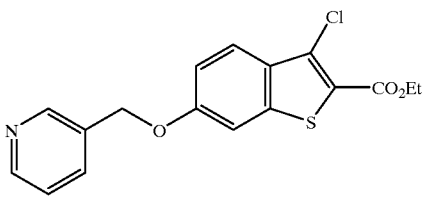

This was prepared by the same procedure as described for Preparation 3, with ethanol instead of methanol.

LRMS (Thermospray): 347.9 (MH$^+$)

$^1$H NMR (300 MHz, CDCl$_3$): δ=1.42 (t, 3H), 4.42 (q, 2H), 5.18 (s, 2H), 7.19 (d, 1H), 7.30–7.38 (m, 2H), 7.80 (d, 1H), 7.88 (d, 1H), 8.62 (d, 1H), 8.73 (s, 1H). $C_{17}H_{14}ClNO_3S$.

Preparation 5

Methyl 3-chloro-5-(3-pyridylmethoxy)benzo[b]thiophene-2-carboxylate

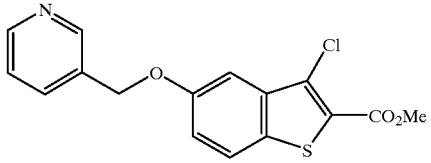

Thionyl chloride (20.3 ml, 279 mmol) was added slowly to a stirred suspension of (E)-3-[3-(3-Pyridylmethoxy)phenyl]-2-propenoic acid (Preparation 2, 14.2 mg, 55.7 mmol) in chlorobenzene (75 ml). The mixture was then heated at reflux for 6 hours before being cooled and poured into methanol (1000 ml). The mixture was heated to reflux for 30 minutes, and after cooling, the solvents were removed under reduced pressure. The residue was partitioned between ethyl acetate and aqueous sodium bicarbonate solution, and the organic layer separated, dried (magnesium sulfate) and evaporated under vacuo. The residue was flash chromatographed on silica gel using a mixture of 90% diethyl ether, and 10% dichloromethane as eluant. The less polar product (first isomer eluted from the chromatography column) was crystallised from diethyl ether to give the title compound as a colourless solid (6.88 g).

m.p. 126–128° C.

LRMS (APCI): 334.8 (MH$^+$)

$^1$H NMR (300 MHz, CDCl$_3$): δ=3.98 (s, 3H), 5.21 (s, 2H), 7.23 (dd, 1H), 7.37 (dd, 1H), 7.45 (d, 1H), 7.71 (d, 1H), 7.83 (d, 1H), 8.63 (d, 1H), 8.76 (s, 1H).

Analysis: Found: C, 57.52; H, 3.57; N, 4.10. $C_{16}H_{12}ClNO_3S$ Requires: C, 57.57; H, 3.62; N, 4.20.

Preparation 6

Methyl 3-chloro-7-(3-pyridylmethoxy)benzo[b]thiophene-2-carboxylate

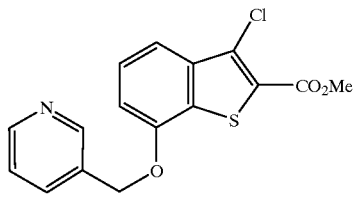

The more polar isomer from the formation of Preparation 5 was isolated by continuation of the flash chromatography to give this title compound which was crystallised from a dichloromethane and hexane mixture to give a colourless solid (2.42 g).

m.p. 144–146° C.

LRMS (APCI): 334.8 (MH+)

$^1$H NMR (300 MHz, CDCl$_3$): δ=3.98 (s, 3H), 5.31 (s, 2H), 7.00 (d, 1H), 7.37 (dd, 1H), 7.45 (t, 1H), 7.62 (d, 1H), 7.85 (d, 1H), 8.63 (d, 1H), 8.76 (s, 1H).

Analysis: Found: C, 56.93; H, 3.56; N, 4.00. C$_{16}$H$_{12}$ClNO$_3$S Requires: C, 57.57; H, 3.62; N, 4.20.

Preparation 7

Ethyl 3-chloro-5-(3-pyridylmethoxy)benzo[b]thiophene-2-carboxylate

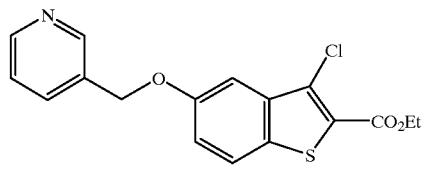

This was prepared by the same procedure as described for Preparation 5, with ethanol instead of methanol.

LRMS (Thermospray): 348.1 (MH+)

$^1$H NMR (300 MHz, CDCl$_3$): δ=1.44 (t, 3H), 4.43 (q, 2H), 5.21 (s, 2H), 7.23 (dd, 1H), 7.37 (dd, 1H), 7.45 (d, 1H), 7.71 (d, 1H), 7.83 (d, 1H), 8.63 (d, 1H), 8.76 (s, 1H).

C$_{17}$H$_{14}$ClNO$_3$S.

Preparation 8

Ethyl 6-(benzyloxy)-3-chlorobenzo[b]thiophene-2-carboxylate

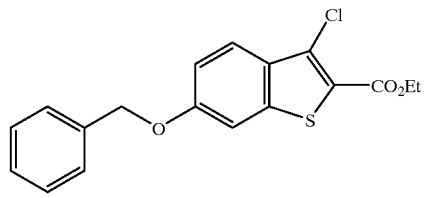

Thionyl chloride (7.3 ml, 100 mmol) was added slowly to a stirred mixture of (E)-3-[4-(benzyloxy)phenyl]-2-propenoic acid (5.08 mg, 20 mmol), pyridine (0.32 ml, 4 mmol) and dimethylformamide (1.5 ml, 20 mmol) in chlorobenzene (20 ml). The mixture was then heated at 130° C. for 24 hours, before being cooled and poured into ethanol (100 ml). The mixture was heated briefly to reflux for 20 minutes and, after cooling, the solvents were removed under reduced pressure. The residue was partitioned between dichloromethane and aqueous ammonium hydroxide solution, and the organic layer separated, dried (magnesium sulfate) and evaporated under vacuo. The residue was flash chromatographed on silica gel using a mixture of 70% hexane and 30% dichloromethane as eluant, and the product was crystallised from diisopropyl ether to give the title compound as a colourless solid (930 mg).

m.p. 98–100° C.

LRMS (Thermospray): 347.0 (MH+)

$^1$H NMR (300 MHz, CDCl$_3$): δ=1.42 (t, 3H), 4.41 (q, 2H), 5.17 (s, 2H), 7.18 (dd, 1H), 7.28–7.50 (m, 6H), 7.86 (d, 1H).

Analysis: Found: C, 62.14; H, 4.33. C$_{18}$H$_{15}$ClO$_3$S Requires: C, 62.33; H, 4.36.

Preparation 9

Ethyl 3-chloro-6-methylbenzo[b]thiophene-2-carboxylate

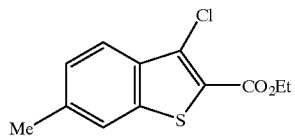

This was prepared by the same procedure as described for Preparation 8, and the product was crystallised from a diethyl ether and hexane mixture.

m.p. 66–68° C.

$^1$H NMR (300 MHz, CDCl$_3$): δ=1.42 (t, 3H), 2.50 (s, 3H), 4.42 (q, 2H), 7.31 (d, 1H), 7.60 (s, 1H), 7.85 (d, 1H).

Analysis: Found: C, 56.40; H, 4.31. C$_{12}$H$_{11}$ClO$_2$S Requires: C, 56.58; H, 4.35.

Preparation 10

Ethyl 6-bromomethyl-3-chlorobenzo[b]thiophene-2-carboxylate

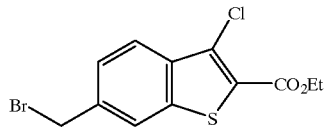

Catalytic azobisisobutylnitrile (AIBN, 0.28 g) and N-bromosuccinimide (4.8 g, 26.8 mmol) were added to a solution of ethyl 3-chloro-6-methylbenzo[b]thiophene-2-carboxylate (Preparation 9, 6.5 g, 25.5 mmol) in tetrachloromethane (50 ml), under a nitrogen atmosphere. The mixture was heated to reflux for 5 hours, cooled, and then loaded onto a silica gel column. The product was eluted with a gradient mixture of dichloromethane and hexane (initially 30:70 increasing to 50:50, and then 70:30). The solvent was removed under reduced pressure to leave the title compound as a colourless solid (8.7 g)

$^1$H NMR (300 MHz, CDCl$_3$): δ=1.42 (t, 3H), 4.42 (q, 2H), 4.61 (s, 2H), 7.50 (d, 1H), 7.82 (s, 1H), 7.93 (d, 1H).

C$_{12}$H$_{10}$BrClO$_2$S

Preparation 11

Ethyl 3-chloro-6-(1H-1-imidazolylmethyl)benzo[b]thiophene2-carboxylate

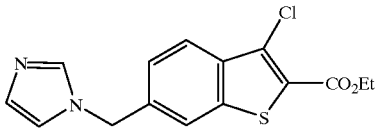

Imidazole (2.0 g, 30 mmol) was added in portions to a stirred suspension of sodium hydride (0.48 g of 60% dispersion in mineral oil, 12 mmol) in anhydrous dimethylformamide (15 ml) at 0° C., under a nitrogen atmosphere. After 40 minutes, ethyl 6-bromomethyl-3-chlorobenzo[b]thiophene-2-carboxylate (Preparation 10, 3.33 g, 10 mmol) was added. After 2 hours the mixture was partitioned between ethyl acetate and water. The organic layer was separated and washed with more water, dried (magnesium sulfate), and evaporated under reduced pressure. The residue was flash chromatographed on silica gel using 5% methanol in dichloromethane as eluant, and the isolated product was crystallised from diethyl ether to give the title compound as a colourless solid (2.02 g).

m.p. 127–129° C.

LRMS (Thermospray): 321.1 (MH+)

$^1$H NMR (300 MHz, CDCl$_3$): δ=1.42 (t, 3H), 4.42 (q, 2H), 5.28 (s, 2H), 6.93 (s, 1H), 7.13 (s, 1H), 7.28 (d, 1H), 7.54 (s, 1H), 7.62 (s, 1H), 7.93 (d, 1H).

Analysis: Found: C, 55.75; H, 4.02; N, 8.61. C$_{15}$H$_{13}$ClN$_2$O$_2$S Requires: C, 56.16; H, 4.08; N, 8.73.

Preparation 12

Ethyl 3-chloro-6-(3H-imidazo[4,5-c]pyridin-3-ylmethyl)benzo[b]thiophene-2-carboxylate

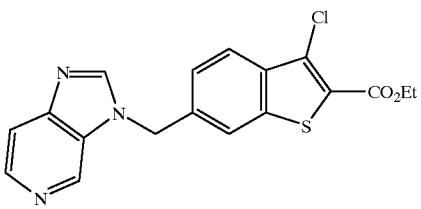

1H-Imidazo[4,5-c]pyridine (536 mg, 4.5 mmol) was added in portions to a stirred suspension of sodium hydride (144 mg of 60% dispersion in mineral oil, 3.6 mmol) in anhydrous dimethylformamide (5 ml) at 0° C., under a nitrogen atmosphere. After 40 minutes, ethyl 6-bromomethyl-3-chlorobenzo[b]thiophene-2-carboxylate (Preparation 10, 1 g, 3 mmol) was added. After 20 hours the mixture was partitioned between ethyl acetate and water. The organic layer was separated and washed with more water, dried (magnesium sulfate), and evaporated under reduced pressure. The residue was flash chromatographed on silica gel using 5% methanol in dichloromethane as eluant The fractions containing the less polar product (first isomer eluted from the chromatography column) were evaporated under reduced pressure to give the title compound as a colourless solid (160 mg).

LRMS (Thermospray): 372.5 (MH+)

$^1$H NMR (300 MHz, CDCl$_3$): δ=1.42 (t, 3H), 4.42 (q, 2H), 5.60 (s, 2H), 7.35 (d, 1H), 7.64 (s, 1H), 7.76 (d, 1H), 7.97 (d, 1H), 8.12 (s, 1H), 8.50 (d, 1H), 8.75 (s, 1H).

The regiochemistry of this isomer was confirmed by an observed nOe difference spectra between the 4-proton of the 3H-Imidazo[4,5-c]pyridin-3-yl group, and the CH$_2$ link. In contrast, the isomer in Preparation 13 displayed an nOe between the 7-proton of the 1 H-Imidazo[4,5-c]pyridin-3-yl group, and the CH$_2$ linker. C$_{18}$H$_{14}$ClN$_3$O$_2$S.

Preparation 13

Ethyl 3-chloro-6-(1H-imidazo[4,5-c]pyridin-1-ylmethyl)benzo[b]thiophene-2-carboxylate

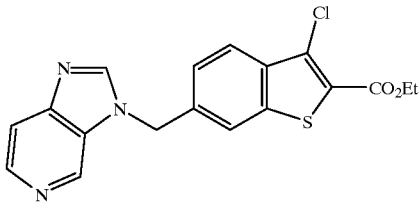

The more polar isomer from the formation of Preparation 12 was isolated by continuation of the flash chromatography to give this title compound as a colourless solid (230 mg).

LRMS (Thermospray): 372.3 (MH+)

$^1$H NMR (300 MHz, CDCl$_3$): δ=1.41 (t, 3H), 4.42 (q, 2H), 5.51 (s, 2H), 7.22 (d, 1H), 7.33 (d, 1H), 7.58 (s, 1H), 7.97 (d, 1H), 8.04 (s, 1H), 8.42 (d, 1H), 9.18 (s, 1H). C$_{18}$H$_{14}$ClN$_3$O$_2$S.

Preparation 14

Ethyl 3-chloro-6-[(methylcarbonyloxy)methyl]benzo[b]thiophene-2-carboxylate

Sodium acetate (3.3 g, 40.5 mmol) was added to a stirred solution of ethyl 6-bromomethyl-3-chlorobenzo[b]thiophene-2-carboxylate (Preparation 10, 4.5 g, 13.5 mmol) in a mixture of anhydrous dimethylformamide (20 ml) and anhydrous tetrahydrofuran (10 ml), under a nitrogen atmosphere. The mixture was heated at 80° C. for 20 hours, then the mixture was partitioned between diethyl ether and water. The organic layer was separated and washed with more water, dried (magnesium sulfate), and evaporated under reduced pressure. The residue was flash chromatographed on silica gel using dichloromethane as eluant to give the title compound as a colourless gum (2.66 g).

$^1$H NMR (300 MHz, CDCl$_3$): δ=1.42 (t, 3H), 2.13 (s, 3H), 4.42 (q, 2H), 5.23 (s, 2H), 7.48 (d, 1H), 7.81 (s, 1H), 7.96 (d, 1H). C$_{14}$H$_{13}$ClO$_4$S.

Preparation 15

Ethyl 3-(chloro)-6-(hydroxymethyl)benzo[b]thiophene-2-carboxylate

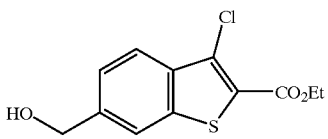

Potassium carbonate (2 g) was added to a stirred solution of ethyl 3-chloro-6-[(methylcarbonyloxy)methyl]benzo[b]thiophene-2-carboxylate (Preparation 14, 2.65 g, 8.5 mmol) in ethanol (40 ml). The mixture was stirred at ambient temperature for 20 hours, then the solvent was removed under reduced pressure. The residue was partitioned between dichloromethane and water. The organic layer was separated and washed with more water, dried (magnesium sulfate), and evaporated under reduced pressure. The residue was flash chromatographed on silica gel using a gradient of 0–2% methanol in dichloromethane as eluant to give the title compound, which was crystallised from diethyl ether to give a colourless solid (1.66 g).

m.p. 117–118° C.
LRMS (APCI): 270.4 (MH$^+$)
$^1$H NMR (300 MHz, CDCl$_3$): δ=1.42 (t, 3H), 1.90 (brs, 1H), 4.42 (q, 2H), 4.88 (s, 2H), 7.47 (d, 1H), 7.83 (s, 1H), 7.95 (d, 1H).
Analysis: Found: C, 52.95; H, 4.02. C$_{12}$H$_{11}$ClO$_3$S Requires: C, 53.24; H, 4.10.

Preparation 16

Ethyl 6-(hydroxymethyl)-3-[(3-methoxyphenyl)sulfanyl]benzo[b]thiophene-2-carboxylate

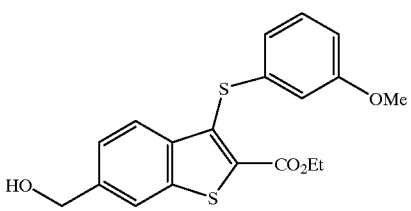

1,8-Diazabicyclo[5.4.0]undec-7-ene (DBU—1.1 ml, 7.23 mmol) was added to a mixture of ethyl 3-(chloro)-6-(hydroxymethyl)benzo[b]thiophene-2-carboxylate (Preparation 15— 1.63 g, 6.02 mmol) and 3-methoxybenzenethiol (1.1 ml, 9.03 mmol) in anhydrous dimethylformamide (8 ml) under a nitrogen atmosphere. The solution was stirred at ambient temperature for 18 hours, and then heated to 60° C. for 3 hours. The solution was partitioned between diethyl ether and water. The organics were separated and washed with water, dried (magnesium sulfate) and evaporated under reduced pressure. The residue was crystallised from diethyl ether and hexane to give the title compound as a colourless solid (1.77 g).

m.p. 110–112° C.
LRMS (Thermospray): 375.1 (MH$^+$)
$^1$H NMR (300 MHz, CDCl$_3$): δ=1.37 (t, 3H), 1.80 (t, 1H), 3.69 (s, 3H), 4.39 (q, 2H), 4.81 (d, 2H), 6.63–6.76 (m, 3H), 7.10 (t, 1H), 7.32 (d, 1H), 7.80 (d, 1H), 7.88 (s, 1H).

Analysis: Found: C, 60.66; H, 4.85. C$_{19}$H$_{18}$O$_4$S$_2$ Requires: C, 60.94; H, 4.85.

Preparation 17

Ethyl 6-(hydroxymethyl)-3-[(3-methoxyphenyl)sulfinyl]benzo[b]thiophene-2-carboxylate

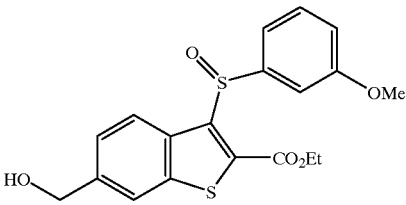

Hydrogen peroxide in water (0.52 ml of 30% w/v, 4.6 mmol) was added to a solution of ethyl 6-(hydroxymethyl)-3-[(3-methoxyphenyl)sulfanyl]benzo[b]thiophene-2-carboxylate (Preparation 16, 1.73 g, 4.6 mmol) in a mixture of acetic acid (20 ml) and ethanol (10 ml). The mixture was heated to 100° C. for 60 minutes. The solvents were removed by evaporation under reduced pressure, and the residue was partitioned between ethyl acetate and aqueous sodium bicarbonate solution. The organic layer was separated, dried (magnesium sulfate) and concentrated under vacuo, and the residue was flash chromatographed on silica gel using 2% ethanol in dichloromethane as eluant. The title compound was isolated as a foam (1.28 g).

LRMS (Thermospray): 391.0 (MH$^+$)
$^1$H NMR (300 MHz, CDCl$_3$): δ=1.43 (t, 3H), 1.85 (t, 1H), 3.80 (s, 3H), 4.48 (q, 2H), 4.89 (d, 2H), 6.90 (d, 1H), 7.25–7.41 (m, 3H), 7.50 (s, 1H), 7.82 (s, 1H), 8.72 (d, 1H). C$_{19}$H$_{18}$O$_5$S$_2$

Preparation 18

Ethyl 3-[(3-methoxyphenyl)sulfinyl]-6-[(methylsulfonyloxy)methyl]benzo[b]thiophene-2-carboxylate

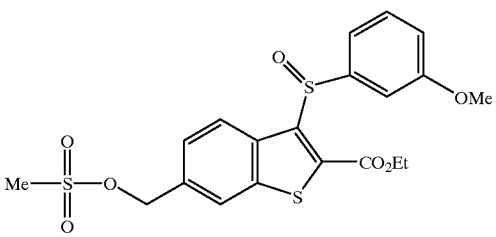

Methanesulfonyl chloride (0.043 ml, 0.55 mmol) was added to a stirred solution of ethyl 6-(hydroxymethyl)-3-[(3-methoxyphenyl)sulfinyl]benzo[b]thiophene-2-carboxylate (Preparation 17, 195 mg, 0.5 mmol) and N-ethyl-N,N-diisopropylamine (0.1 ml, 0.55 mmol) in dichloromethane (3 ml) at 0° C. After 3 hours the solution was washed twice with water, dried (magnesium sulfate), and the solvent removed under reduced pressure. The residue was crystallised from diethyl ether to give the title compound as a colourless solid (155 mg).

m.p. 80–83° C.
$^1$H NMR (300 MHz, CDCl$_3$): δ=1.45 (t, 3H), 2.96 (s, 3H), 3.81 (s, 3H), 4.50 (q, 2H), 5.32 (s, 2H), 6.93 (dd, 1H), 7.30–7.43 (m, 3H), 7.50 (s, 1H), 7.88 (s, 1H), 8.80 (d, 1H). C$_{20}$H$_{20}$O$_7$S$_3$

Preparation 19

Ethyl 6-(hydroxy)-3-(phenylsulfinyl)benzo[b]thiophen-2-carboxylate

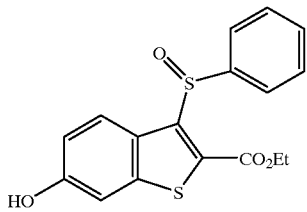

Trifluoroacetic acid (50 ml) was added to a stirred mixture of ethyl 6-(benzyloxy)-3-(phenylsulfinyl)benzo[b]thiophene-2-carboxylate (Example 31, 4.9 g, 11.2 mmol) and methyl phenyl sulfide (5.2 ml, 45 mmol) at ambient temperature under a nitrogen atmosphere. After 20 hours the solvents were removed under reduced pressure, and the residue was azeotroped using toluene. The residue was flash chromatographed on silica gel using 2% ethanol in dichloromethane as eluant. The isolated product was crystallised from diisopropyl ether to give the title compound as a colourless solid (3.05 g).

m.p. 185–187° C.

LRMS (Thermospray): 347.4 (MH$^+$)

$^1$H NMR (300 MHz, DMSO-d$_6$): δ=1.33 (t, 3H), 4.40 (q, 2H), 6.92 (dd, 1H), 7.36 (s, 1H), 7.42–7.58 (m, 3H), 7.79 (d, 2H), 8.41 (d, 1H), 10.25 (brs, 1H).

Analysis: Found: C, 58.76; H, 4.03. C$_{17}$H$_{14}$O$_4$S$_2$ Requires: C, 58.94; H, 4.07.

Example 1

Ethyl 3-(phenylsulfanyl)-6-(3-pyridylmethoxy)benzo[b]thiophene-2-carboxylate

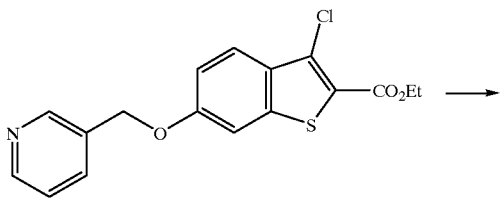

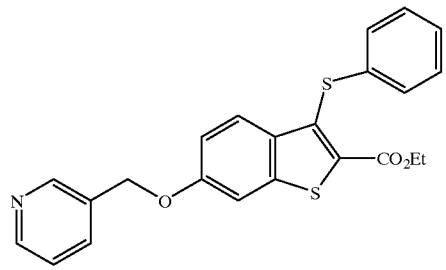

1,8-Diazabicyclo[5.4.0]undec-7-ene (DBU—1.46 ml, 9.5 mmol) was added to a mixture of ethyl 3-chloro-6-(3-pyridylmethoxy)benzo[b]thiophene-2-carboxylate (Preparation 4, 3.0 g, 8.6 mmol) and thiophenol (1.76 ml, 17.2 mmol) in dimethylformamide (15 ml) under a nitrogen atmosphere. The solution was heated to 60° C. for 5 hours and then partitioned between diethyl ether and water. The organics were separated and washed with water, dried (magnesium sulfate) and evaporated under reduced pressure. The residue was flash chromatographed on silica gel using diethyl ether, and then ethyl acetate, as eluant. The isolated product was crystallised from diethyl ether and hexane to give the title compound as a colourless solid (2.85 g).

m.p. 94–95° C.

LRMS (Thermospray): 422.2 (MH$^+$)

$^1$H NMR (300 MHz, CDCl$_3$): δ=1.33 (t, 3H), 4.36 (q, 2H), 5.13 (s, 2H), 7.00 (dd, 1H), 7.06–7.24 (m, 5H), 7.30–7.37 (m, 2H), 7.70 (d, 1H), 7.78 (d, 1H), 8.60 (d, 1H), 8.70 (s, 1H).

Analysis: Found: C, 65.23; H, 4.50; N, 3.28. C$_{23}$H$_{19}$NO$_3$S$_2$ Requires: C, 65.53; H, 4.54; N, 3.32.

Examples 2–15

These were prepared by the method of Example 1, using the appropriate substituted thiophenol and benzo[b]thiophene starting materials as described in Preparations 3, 4, 5 or 7.

Their physical data are shown in Table 1 and Table 2.

TABLE 1

[Structure: benzothiophene core with pyridin-3-ylmethoxy group at 6-position, X-R¹ at 3-position, and C(O)-O-R³ at 2-position]

| Example N° | X-R¹ (substituent) | R³ | Physical Data |
|---|---|---|---|
| 2 | 5-(methylthio)-1,3-benzodioxole (S-linked) | Me | m.p. 126–128° C.<br>LRMS(Thermospray): 452.3(MH⁺)<br>¹H NMR(300 MHz, CDCl₃): δ = 3.84(s, 3H), 5.14(s, 2H), 5.90(s, 2H), 6.66(d, 1H), 6.74(s, 1H), 6.86(d, 1H), 7.02(dd, 1H), 7.34(m, 2H), 7.77(m, 2H), 8.60(d, 1H), 8.71(s, 1H).<br><br>Analysis: Found: C, 61.18; H, 3.80, N, 3.10.<br>C₂₃H₁₇NO₅S₂ Requires: C, 60.96; H, 4.82; N, 3.03. |
| 3 | 3-methoxyphenylthio | Et | m.p. 85–86° C. (from diethyl ether/hexane)<br>LRMS(APCI): 451.9(MH⁺)<br>¹H NMR(300 MHz, CDCl₃): δ = 1.36(t, 3H), 3.70(s, 3H), 4.38(q, 2H), 5.13(s, 2H), 6.65(dd, 1H), 6.70–6.75 (m, 2H), 7.02(dd, 1H), 7.10(t, 1H), 7.35(m, 2H), 7.70 (d, 1H), 7.78(d, 1H), 8.60(d, 1H), 8.71(s, 1H).<br><br>Analysis: Found: C, 63.57; H, 4.68, N, 3.10.<br>C₂₄H₂₁NO₄S₂ Requires: C, 63.83; H, 4.69; N, 3.10. |
| 4 | 2-methylphenylthio | Et | LRMS(Thermospray): 435.8(MH⁺)<br>¹H NMR(300 MHz, CDCl₃): δ = 1.33(t, 3H), 2.47(s, 3H), 4.38(q, 2H), 5.14(s, 2H), 6.80(d, 1H), 6.90–7.10 (m, 3H), 7.17(d, 1H), 7.33–7.38(m, 2H), 7.59(d, 1H), 7.78(d, 1H), 8.61(d, 1H), 8.70(s, 1H).<br><br>Analysis: Found: C, 65.95; H, 4.85, N, 3.21.<br>C₂₄H₂₁NO₃S₂ Requires: C, 66.18; H, 4.86; N, 3.22. |
| 5 | 2-hydroxyphenylthio | Et | m.p. 172–174° C. (from ethyl acetate)<br>LRMS(Thermospray): 438.2(MH⁺)<br>¹H NMR(300 MHz, DMSO-d₆): δ = 1.24(t, 3H), 4.30(q, 2H), 5.20(s, 2H), 6.57–6.67(m, 2H), 6.80(d, 1H), 6.98 (t, 1H), 7.06(d, 1H), 7.40(dd, 1H), 7.55(d, 1H), 7.75(s, 1H), 7.87(d, 1H), 8.54(d, 1H), 8.67(s, 1H), 10.02(s, 1H).<br><br>Analysis: Found: C, 63.35; H, 4.29, N, 3.13.<br>C₂₃H₁₉NO₄S₂ Requires: C, 63.14; H, 4.38; N, 3.20. |
| 6 | 2-methoxyphenylthio | Et | LRMS(Thermospray): 452.1(MH⁺)<br>¹H NMR(300 MHz, CDCl₃): δ = 1.33(t, 3H), 3.89(s, 3H), 4.36(q, 2H), 5.13(s, 2H), 6.70(m, 2H), 6.85(d, 1H), 7.01(dd, 1H), 7.10(m, 1H), 7.30–7.38(m, 2H), 7.70–7.80(m, 2H), 8.60(d, 1H), 8.72(s, 1H).<br>C₂₄H₂₁NO₄S₂ |
| 7 | 2-chlorophenylthio | Et | m.p. 137–139° C.<br>LRMS(Thermospray): 456.6(MH⁺)<br>¹H NMR(300 MHz, CDCl₃): δ = 1.30(t, 3H), 4.36(q, 2H), 5.18(s, 2H), 6.64(d, 1H), 6.90–7.10(m, 3H), 7.30–7.40(m, 3H), 7.75(d, 1H), 7.80(d, 1H) 8.62(br, 1H), 8.73(br, 1H).<br>C₂₃H₁₁ClNO₃S₂ |

TABLE 1-continued

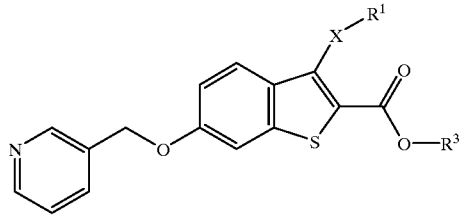

| Example N° | X–R¹ | R³ | Physical Data |
|---|---|---|---|
| 8 | 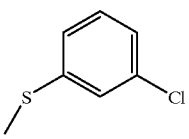 | Et | m.p. 114–116° C.<br>LRMS(Thermospray): 456.6(MH⁺)<br>¹H NMR(300 MHz, CDCl₃): δ = 1.34(t, 3H), 4.38(q, 2H), 5.18(s, 2H), 6.98–7.13(m, 5H), 7.30–7.40(m, 2H), 7.75(d, 1H), 7.80(d, 1H) 8.62(br.d, 1H), 8.72(br.s, 1H).<br>$C_{23}H_{18}ClNO_3S_2$ |
| 9 | 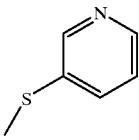 | Et | m.p. 108–110° C.<br>LRMS(Thermospray): 423.0(MH⁺)<br>¹H NMR(300 MHz, CDCl₃): δ = 1.36(t, 3H), 4.38(d, 2H), 5.18(s, 2H), 7.03–7.15(m, 2H), 7.30–7.50(m, 3H), 7.75–7.81(m, 2H), 8.38(d, 1H), 8.43(s, 1H), 8.62(d, 1H), 8.72(s, 1H).<br>$C_{22}H_{18}N_2O_3S_2$ |
| 10 | 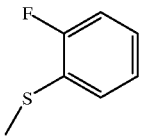 | Et | m.p. 85° C. (from diisopropyl ether)<br>LRMS(Thermospray): 440.4(MH⁺)<br>¹H NMR(400 MHz, CDCl₃): δ = 1.30(t, 3H), 4.33(q, 2H), 5.13(s, 2H), 6.85–7.15(m, 5H), 7.30(m, 2H), 7.75 (m, 2H), 8.58(d, 1H), 8.67(s, 1H).<br>$C_{23}H_{18}FNO_3S_2$ |
| 11 | 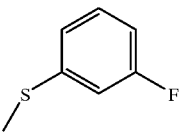 | Et | m.p. 110° C. (from diisopropyl ether)<br>¹H NMR(400 MHz, CDCl₃): δ = 1.30(t, 3H), 4.35(q, 2H), 5.12(s, 2H), 6.78(m, 2H), 6.90(d, 1H), 7.03(d, 1H), 7.14(m, 1H), 7.32(m, 2H), 7.70–7.80(m, 2H), 8.58 (d, 1H), 8.69(s, 1H).<br>$C_{23}H_{18}FNO_3S_2$ |
| 12 | 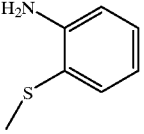 | Et | m.p. 103–105° C. (from diethyl ether/hexane)<br>LRMS(Thermospray): 437.3(MH⁺)<br>¹H NMR(300 MHz, DMSO-d₆): δ = 1.32(t, 3H), 4.35(q, 2H), 5.20(s, 2H), 5.44(s, 2H), 6.48(t, 1H), 6.68(d, 1H), 6.98–7.07(m, 2H), 7.20(d, 1H), 7.40(dd, 1H), 7.61(d, 1H), 7.70(s, 1H), 7.85(d, 1H), 8.53(d, 1H), 8.66(s, 1H).<br>$C_{23}H_{20}N_2O_3S_2$ |
| 13 | 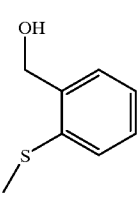 | Et | LRMS(Thermospray): 452.0(MH⁺).<br>¹H NMR(400 MHz, CDCl₃): δ = 1.33(t, 3H), 2.73(brs, 1H), 4.35(q, 2H), 4.90(s, 2H), 5.18(s, 2H), 6.89(d, 1H), 7.03–7.10(m, 2H), 7.19(t, 1H), 7.32–7.40(m, 2H), 7.43(d, 1H), 7.77–7.83(m, 2H), 8.63(2, 1H), 8.73(s, 1H).<br>$C_{24}H_{21}NO_4S_2$ |

TABLE 2

| Example N° | X-R¹ | R³ | Physical Data |
|---|---|---|---|
| 14 | (phenylsulfanylmethyl) | Me | LRMS(APCI): 408.2(MH⁺)<br>¹H NMR(400 MHz, DMSO-d₆): δ = 3.75(s, 3H), 5.02(s, 2H), 7.16–7.33(m, 7H), 7.38(m, 1H), 7.77(d, 1H), 8.02 (d, 1H), 8.51(d, 1H), 8.60(s, 1H).<br>C₂₂H₁₇NO₃S₂ |
| 15 | (2-methyl-phenylsulfanylmethyl) | Et | m.p. 95° C. (from diethyl ether)<br>LRMS(Thermospray): 436.2(MH⁺)<br>¹H NMR(300 MHz, CDCl₃): δ = 1.35(t, 3H), 2.46(s, 3H), 4.38(q, 2H), 4.84(s, 2H), 6.88(d, 1H), 6.98(t, 1H), 7.09(t, 1H), 7.12–7.20(m, 3H), 7.28(m, 1H), 7.67(d, 1H), 7.74(d, 1H), 8.60(m, 2H).<br><br>Analysis: Found: C, 66.07; H, 4.81, N, 3.15.<br>C₂₄H₂₁NO₃S₂ Requires: C, 66.18; H, 4.86; N, 3.22. |

Example 16

Ethyl 3-[2-(N,N-dimethylsulfonylamino)phenyl]sulfanyl-6-(3-pyridylmethoxy)benzo[b]thiophene-2-carboxylate

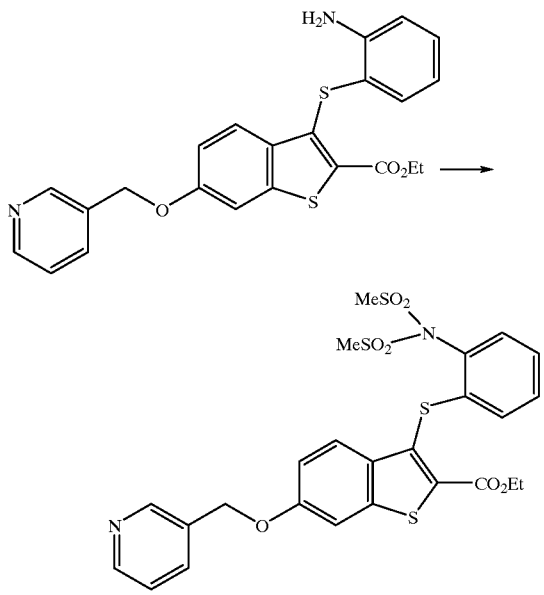

Methanesulfonyl chloride (0.86 ml, 1.1 mmol) was added to a stirred solution of ethyl 3-[(2-aminophenyl)sulfanyl]-6-(3-pyridylmethoxy)benzo[b]thiophene-2-carboxylate (Example 12 220 mg, 0.5 mmol) and N,N-diisopropylethylamine (0.2 ml, 1.1 mmol) in dichloromethane (3 ml). The mixture was left at ambient temperature for 20 hours and then diluted with dichloromethane and washed with water. The organics were dried (magnesium sulfate), and evaporated under reduced pressure. The residue was flash chromatographed on silica gel using diethyl ether, and then ethyl acetate, as eluant. The title product was crystallised from diethyl ether to give a colourless solid (232 mg).

m.p. 165–167° C.

LRMS (Thermospray): 593.5 (MH⁺)

¹H NMR (300 MHz, CDCl₃): δ=1.33 (t, 3H), 3.63 (s, 6H), 4.36 (q, 2H), 5.14 (s, 2H), 6.66 (d, 1H), 7.03 (dd, 1H), 7.10–7.20 (m, 2H), 7.30–7.39 (m, 3H), 7.70–7.80 (m, 2H), 8.60 (d, 1H), 8.70 (s, 1H). C₂₅H₂₄N₂O₇S₄

Example 17

Ethyl 6-(benzyloxy)-3-(phenylsulfanyl)benzo[b]thiophene-2-carboxylate

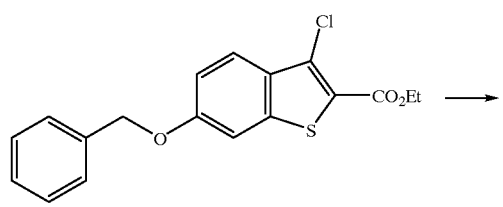

-continued

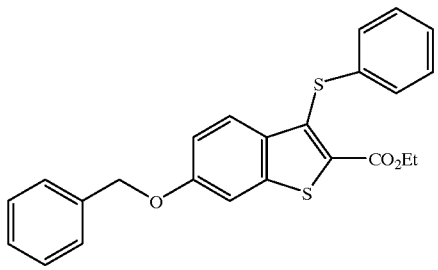

1,8-Diazabicyclo[5.4.0]undec-7-ene (DBU—0.39 ml, 2.5 mmol) was added to a mixture of ethyl 6-(benzyloxy)-3-chlorobenzo[b]thiophene-2-carboxylate (Preparation 8, 800 mg, 2.3 mmol) and thiophenol (0.47 ml, 4.6 mmol) in dimethylformamide (4 ml) under a nitrogen atmosphere. The solution was heated to 60° C. for 6 hours and then partitioned between diethyl ether and water. The organics were separated and washed with water, dried (magnesium sulfate) and evaporated under reduced pressure. The residue was flash chromatographed on silica gel using a mixture of 20% dichloromethane and 80% hexane, then 50% dichloromethane and 50% hexane as eluant. The isolated product was crystallised from diisopropyl ether and hexane to give the title compound as a colourless solid (810 mg).

m.p. 96–97° C.

$^1$H NMR (300 MHz, CDCl$_3$): δ=1.36 (t, 3H), 4.35 (q, 2H), 5.13 (s, 2H), 7.02 (dd, 1H), 7.10–7.24 (m, 5H), 7.30–7.50 (m, 6H), 7.70 (d, 1H).

Analysis: Found: C, 68.16; H, 4.74. C$_{24}$H$_{20}$O$_3$S$_2$ Requires: C, 68.54; H, 4.79.

Example 18
Ethyl 6-(1H-1-imidazolylmethyl)-3-[(3-methoxyphenyl)sulfanyl]benzo[b]thiophene-2-carboxylate

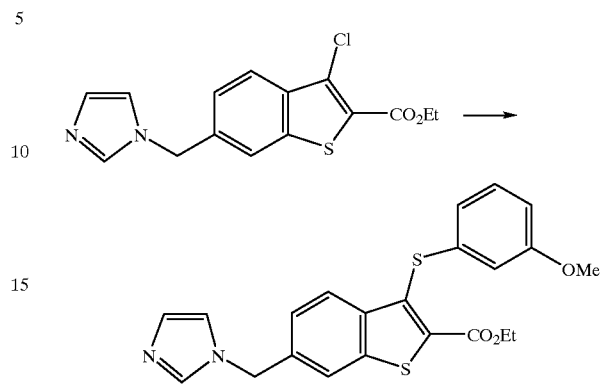

1,8-Diazabicyclo[5.4.0]undec-7-ene (DBU—0.26 ml, 1.7 mmol) was added to a mixture of ethyl 3-chloro-6-(1H-1-imidazolylmethyl)benzo[b]thiophene-2-carboxylate (Preparation 11, 500 mg, 1.6 mmol) and 3-methoxybenzenethiol (0.29 ml, 2.3 mmol) in dimethylformamide (2 ml) under a nitrogen atmosphere. The solution was heated to 60° C. for 5 hours and then partitioned between ethyl acetate and water. The organics were separated and washed with water, dried (magnesium sulfate) and evaporated under reduced pressure. The residue was flash chromatographed on silica gel using 5% methanol in dichloromethane as eluant to give the title compound as a gum (615 mg).

LRMS (Thermospray): 424.7 (MH$^+$)

$^1$H NMR (400 MHz, CDCl$_3$): δ=1.38 (t, 3H), 3.70 (s, 3H), 4.40 (q, 2H), 5.27 (s, 2H), 6.65–6.75 (m, 3H), 6.94 (s, 1H), 7.08–7.19 (m, 3H), 7.60 (s, 1H), 7.72 (s, 1H), 7.80 (d, 1H). C$_{22}$H$_{20}$N$_2$O$_3$S$_2$

Examples 19–21

These were prepared by the method of Example 18, using the appropriate substituted thiophenol and benzo[b]thiophene starting materials. Their physical data are shown in Table 3.

TABLE 3

| Example N° | X−R$^1$ / | R$^3$ | Physical Data |
|---|---|---|---|
| 19 | HO-phenyl-S- (2-hydroxy) | Et | LRMS(Thermospray): 411.3(MH$^+$)<br>$^1$H NMR(300 MHz, CDCl$_3$): δ = 1.42(t, 3H), 4.48(q, 2H), 5.22 (s, 2H), 6.80(t, 1H), 6.87–6.95(m, 2H), 7.10(s, 1H), 7.16–7.28 (m, 2H), 7.50(s, 1H), 7.55(s, 1H), 7.70(d, 1H), 8.22(d, 1H), 8.60(brs, 1H).<br>C$_{21}$H$_{18}$N$_2$O$_3$S$_2$ |

TABLE 3-continued

| Example N° | X-R¹ | R³ | Physical Data |
|---|---|---|---|
| 20 | HO-phenyl-S- | Me | m.p. 188–190° C. (from methanol)<br>LRMS(Thermospray): 397.2(MH⁺)<br>$^1$H NMR(300 MHz, DMSO-d$_6$): δ = 3.82(s, 3H), 5.30(s, 2H), 6.60(t, 1H), 6.67(d, 1H), 6.80(d, 1H), 6.90(s, 1H), 7.00(t, 1H), 7.20(s, 1H), 7.25(d, 1H), 7.62(d, 1H), 7.77(s, 1H), 7.92 (s, 1H), 10.03(s, 1H).<br>$C_{20}H_{16}N_2O_3S_2$ |
| 21 | Me-phenyl-S- | Et | m.p. 88–89° C. (from diethyl ether/hexane)<br>LRMS(Thermospray): 409.2(MH⁺)<br>$^1$H NMR(300 MHz, CDCl$_3$): δ = 1.34(t, 3H), 2.46(s, 3H), 4.36 (q, 2H), 5.22(s, 2H), 6.80(d, 1H), 6.88–6.98(m, 2H), 7.00–7.20 (m, 4H), 7.55(s, 1H), 7.59(s, 1H), 7.63(d, 1H).<br><br>Analysis: Found: C, 64.34; H, 4.91, N, 6.74.<br>$C_{22}H_{20}N_2O_2S_2$ Requires: C, 64.68; H, 4.93; N, 6.86. |

Example 22

Ethyl 6-(3H-imidazo[4,5-c]pyridin-3-ylmethyl)-3-[(3-methoxyphenyl)sulfanyl]benzo[b]thiophene-2-carboxylate

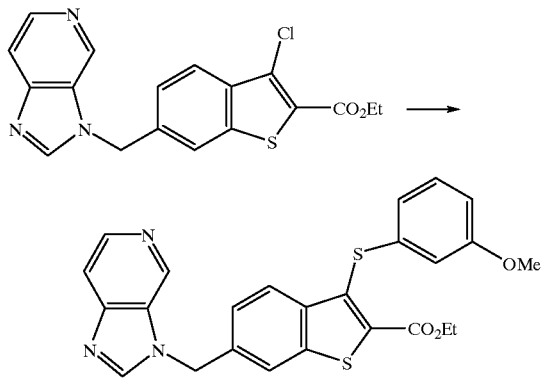

1,8-Diazabicyclo[5.4.0]undec-7-ene (DBU—0.07 ml, 0.48 mmol) was added to a mixture of ethyl 3-(chloro)-6-(3H-imidazo[4,5-c]pyridin-3-ylmethyl)benzo[b]thiophene-2 carboxylate (Preparation 12, 150 mg, 0.4 mmol) and 3-methoxybenzenethiol (0.07 ml, 0.6 mmol) in a mixture of dimethylformamide (1 ml) and tetrahydrofuran (1 ml) under a nitrogen atmosphere. The solution was heated to 60° C. for 6 hours and then partitioned between ethyl acetate and water. The organics were separated and washed with water, dried (magnesium sulfate) and evaporated under reduced pressure. The residue was triturated with diethyl ether and hexane mixture to give the title compound as a colourless solid (155 mg).

LRMS (Thermospray): 476.3 (MH⁺)

$^1$H NMR (300 MHz, CDCl$_3$): δ=1.38 (t, 3H), 3.68 (s, 3H), 4.39 (q, 2H), 5.55 (s, 2H), 6.63–6.75 (m, 3H), 7.10 (t, 1H), 7.19 (d, 1H), 7.65 (s, 1H), 7.74 (d, 1H), 7.81 (d, 1H), 8.08 (s, 1H), 8.48 (d, 1H), 8.75 (s, 1H). $C_{25}H_{21}N_3O_3S_2$

Example 23

Ethyl 6-(1H-imidazo[4,5-c]pyridin-1-ylmethyl)-3-[(3-methoxyphenyl)sulfanyl]benzo[b]thiophene-2-carboxylate

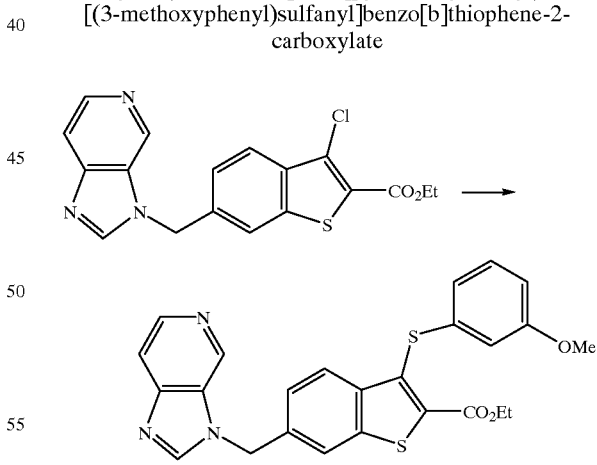

This example was prepared from the intermediate of Preparation 13, using the same method as described for Example 22, to give the title compound as a colourless solid.

LRMS (Thermospray): 476.3 (MH⁺)

$^1$H NMR (300 MHz, CDCl$_3$): δ=1.37 (t, 3H), 3.68 (s, 3H), 4.38 (q, 2H), 5.49 (s, 2H), 6.63–6.75 (m, 3H), 7.10 (t, 1H), 7.15 (d, 1H), 7.23 (d, 1H), 7.60 (s, 1H), 7.80 (d, 1H), 8.01 (s, 1H), 8.42 (d, 1H), 9.18 (s, 1H). $C_{25}H_{21}N_3O_3S_2$

Example 24

Ethyl 3-(phenoxy)-6-(3-pyridylmethoxy)benzo[b]thiophen-2-carboxylate

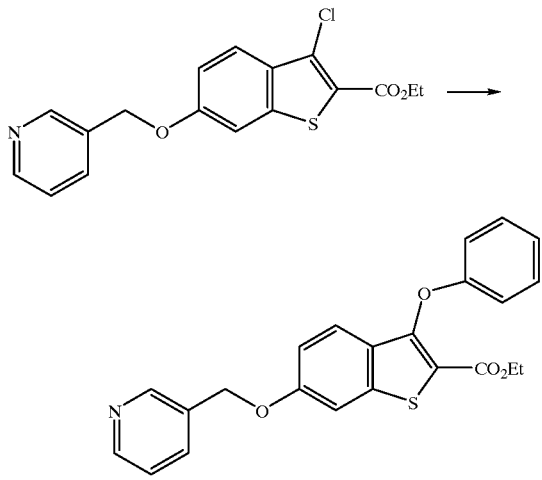

Phenol (108 mg, 1.15 mmol) was added to a stirred suspension of sodium hydride (46 mg of 60% dispersion in mineral oil, 1.15 mmol) in anhydrous dimethylformamide (1 ml), under a nitrogen atmosphere. Ethyl 3-chloro-6-(3-pyridylmethoxy)benzo[b]thiophene-2-carboxylate (Preparation 4, 200 mg, 0.58 mmol) was added to the mixture after 30 minutes, and the mixture was then heated to 75° C. for 48 hours. The reaction was partitioned between ethyl acetate and water. The organics were separated and washed with water, dried (magnesium sulfate) and evaporated under reduced pressure. The residue was flash chromatographed on silica gel using diethyl ether as eluant. The isolated product was crystallised from hexane to give the title compound as a colourless solid (40 mg).

LRMS (Thermospray): 406.5 (MH$^+$)

$^1$H NMR (300 MHz, CDCl$_3$): δ=1.18 (t, 3H), 4.23 (q, 2H), 5.17 (s, 2H), 6.93 (d, 2H), 6.98–7.08 (m, 2H), 7.22–7.40 (m, 4H), 7.57 (d, 1H), 7.80 (d, 1H), 8.62 (d, 1H), 8.71 (s, 1H). C$_{23}$H$_{19}$NO$_4$S.

Example 25 & 26

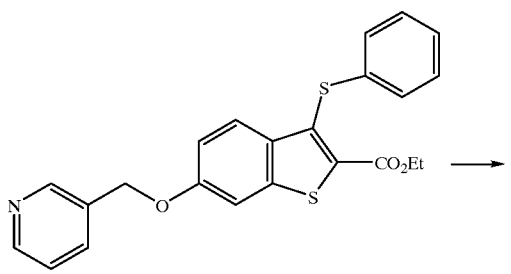

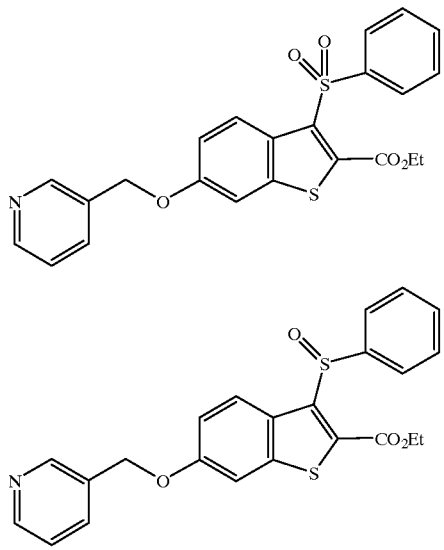

Example 25

Ethyl 3-(phenylsulfonyl)-6-(3-pyridylmethoxy)benzo[b]thiophene-2-carboxylate

Hydrogen peroxide in water (0.42 ml of 30% w/v, 3.75 mmol) was added to a solution of ethyl 3-(phenylsulfanyl)-6-(3-pyridylmethoxy)benzo[b]thiophene-2-carboxylate (Example 1, 633 mg, 1.5 mmol) in acetic acid (4.5 ml). The mixture was heated to 100° C. for 90 minutes. The solvents were removed by evaporation under reduced pressure, and the residue was partitioned between ethyl acetate and aqueous sodium bicarbonate solution. The organic layer was separated, dried (magnesium sulfate) and concentrated under vacuo, and the residue flash chromatographed on silica gel using 1% methanol in dichloromethane as eluant. The less polar product was isolated and crystallised from dichloromethane and diethyl ether to give the title compound as a colourless solid (230 mg).

m.p. 120–122° C.

LRMS (Thermospray): 454.1 (MH$^+$)

Analysis: Found: C, 60.93; H, 4.43; N, 2.98. C$_{23}$H$_{19}$NO$_5$S$_2$ Requires: C, 60.91; H, 4.22; N, 3.09.

$^1$H NMR (300 MHz, CDCl$_3$): δ=1.41 (t, 3H), 4.44 (q, 2H), 5.15 (s, 2H), 7.22 (dd, 1H), 7.27–7.38 (m, 2H), 7.48–7.60 (m, 3H), 7.78 (d, 1H), 8.18 (d, 2H), 8.49 (d, 1H), 8.60 (d, 1H), 8.70 (s, 1H).

Example 26

Ethyl 3-(phenylsulfinyl)-6-(3-pyridylmethoxy)benzo[b]thiophene-2-carboxylate

The more polar product from the previous reaction was isolated by continuation of the flash chromatography to give this title compound which was crystallised from dichloromethane and diethyl ether to give a colourless solid (220 mg).

m.p. 118–120° C.

LRMS (Thermospray): 438.1 (MH$^+$)

Analysis: Found: C, 62.94; H, 4.28; N, 3.52. C$_{23}$H$_{19}$NO$_4$S$_2$ Requires: C, 63.14; H, 4.38; N, 3.20.

$^1$H NMR (300 MHz, CDCl$_3$): δ=1.42 (t, 3H), 4.43 (q, 2H), 5.11 (s, 2H), 7.07 (dd, 1H), 7.24–7.50 (m, 5H), 7.77 (d, 1H), 7.89 (d, 2H), 8.60 (d, 1H), 8.67 (s, 1H), 8.70 (d, 1H).

Examples 27–29

These were prepared by the method of Example 26, using the appropriately substituted 3-arylsulfanyl-benzo[b]thiophene starting materials from Table 1, except that only 1.2 equivalents of hydrogen peroxide were used, to maximise the yield of the sulfinyl analogue. Their physical data are shown in Table 4.

TABLE 4

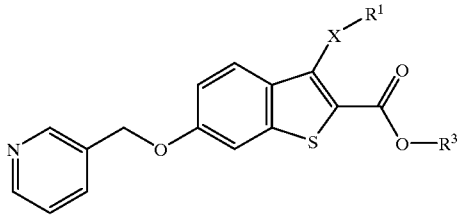

| Example N° | X—R¹ | R³ | Physical Data |
|---|---|---|---|
| 27 | 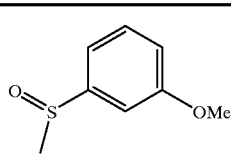 | Et | m.p. 132–134° C. (from diethyl ether)<br>LRMS(Thermospray): 468.5(MH⁺)<br>¹H NMR(300 MHz, CDCl₃): δ = 1.42(t, 3H), 3.82(s, 3H), 4.45(q, 2H), 5.13(s, 2H), 6.92(dd, 1H), 7.07(dd, 1H), 7.28–7.43(m, 4H), 7.50(s, 1H), 7.78(d, 1H), 8.60 (d, 1H), 8.68(s, 1H), 8.70(d, 1H).<br><br>Analysis: Found: C, 61.26; H, 4.47; N, 2.94.<br>C₂₄H₂₁NO₅S₂ Requires: C, 61.66; R, 4.53; N, 3.00. |
| 28 | 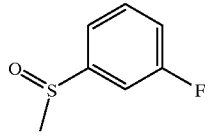 | Et | m.p. 135–137° C. (from diisopropyl ether)<br>LRMS(Thermospray): 455.7(MH⁺)<br>¹H NMR(400 MHz, CDCl₃): δ = 1.40(t, 3H), 4.42(m, 2H), 5.09(s, 2H), 7.05(m, 2H), 7.20–7.40(m, 3H), 7.57–7.75(m, 3H), 8.58–8.68(m, 3H).<br>C₂₃H₁₈FNO₄S₂. |
| 29 | 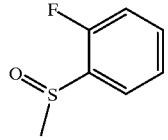 | Et | m.p. 150–151° C. (from diisopropyl ether)<br>LRMS(Thermospray): 456.1(MH⁺)<br>¹H NMR(400 MHz, CDCl₃): δ = 1.38(t, 3H), 4.40(m, 2H), 5.12(s, 2H), 6.96–7.05(m, 2H), 7.26–7.42(m, 4H), 7.73(d, 1H), 8.00(dd, 1H), 8.52–8.60(m, 2H), 8.66(s, 1H).<br>C₂₃H₁₈FNO₄S₂. |

Example 30

Methyl 3-(phenylsulfinyl)-5-(3-pyridylmethoxy) benzo[b]thiophene-2-carboxylate

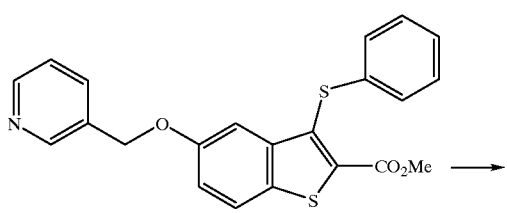 ⟶ 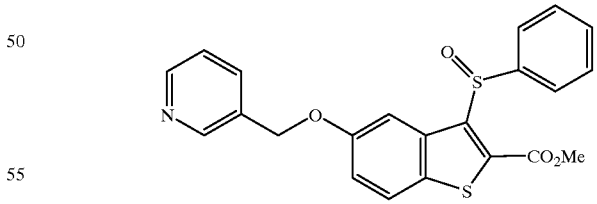

This example was prepared using the same method as described for Example 26, using the 3-(phenylsulfanyl)benzo[b]thiophene derivative from Example 14.

LRMS (APCI): 424.0 (MH⁺)

¹H NMR (400 MHz, DMSO-d₆): δ=3.96 (s, 3H), [5.10 (d, 1H)/5.09 (d, 1H) non-equivalent OC$\underline{H}_2$Py³], 7.31 (d, 1H), 7.42 (dd, 1H), 7.45–7.55 (m, 3H), 7.77 (d, 2H), 7.86 (d, 1H), 8.03 (d, 1H), 8.17 (s, 1H), 8.57 (d, 1H), 8.68 (s, 1H). C₂₂H₁₇NO₄S₂

Example 31

Ethyl 6-(benzyloxy)-3-(phenylsulfinyl)benzo[b]thiophene2-carboxylate

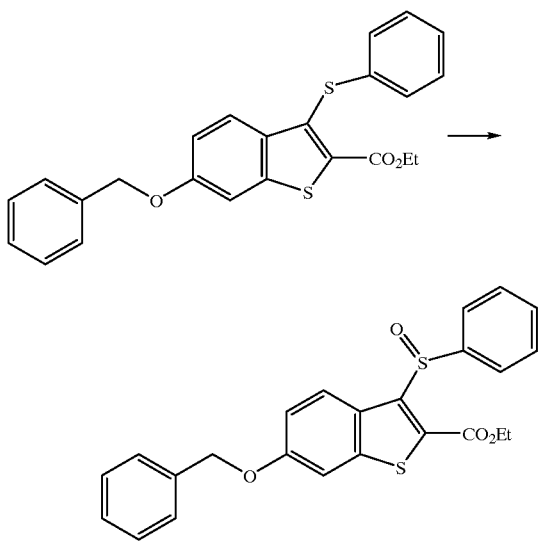

Hydrogen peroxide in water (0.15 ml of 30% w/v, 1.3 mmol) was added to a solution of ethyl 6-(benzyloxy)-3-(phenylsulfanyl)benzo[b]thiophene-2-carboxylate (Example 17— 500 mg, 1.2 mmol) in acetic acid (5 ml) and tetrahydrofuran (5 ml). The mixture was heated to 100° C. for 3 hours. The solvents were removed by evaporation under reduced pressure, and the residue was partitioned between diethyl ether and aqueous sodium bicarbonate solution. The organic layer was separated, dried (magnesium sulfate) and concentrated under vacuo, and the residue was crystallised from dichloromethane and diisopropyl ether to give the title compound as a colourless solid (455 mg).

m.p. 141–142° C.

Analysis: Found: C, 65.74; H, 4.54. $C_{24}H_{20}O_4S_2$ Requires: C, 66.03; H, 4.62.

$^1$H NMR (300 MHz, CDCl$_3$): δ=1.43 (t, 3H), 4.47 (q, 2H), 5.10 (s, 2H), 7.08 (dd, 1H), 7.27–7.53 (m, 9H), 7.90 (d, 2H), 8.70 (d, 1H).

Examples 32–34

These were prepared by the method of Example 31, using the appropriate 3-(phenylsufanyl)benzo[b]thiophene derivatives from Examples 18, 19 and 21. Their physical data are shown in Table 5.

TABLE 5

| Example N° | X–R¹ | R³ | Physical Data |
|---|---|---|---|
| 32 | 3-MeO-C₆H₄-S(O)-Me (structure) | Et | m.p. 149–151° C. (from diethyl ether)<br>LRMS(Thermospray): 441.3(MH⁺)<br>$^1$H NMR(300 MHz, CDCl$_3$): δ = 1.43(t, 3H), 3.80(s, 3H), 4.47(q, 2H), 5.21(s, 2H), 6.85–6.95(m, 2H), 7.10 (s, 1H), 7.19(d, 1H), 7.30–7.40(m, 2H), 7.45–7.53(m, 2H), 7.58(s, 1H), 8.74(d, 1H).<br>$C_{22}H_{20}N_2O_4S_2$ |
| 33 | 2-HO-C₆H₄-S(O)-Me (structure) | Et | m.p. 195–196° C. (from ethyl acetate)<br>HRMS(+ve ion electrospray): 427.1(MH⁺)<br>$^1$H NMR(300 MHz, DMSO-d$_6$): δ = 1.34(t, 3H), 4.39(q, 2H), 5.26(s, 2H), 6.73(d, 1H), 6.89(s, 1H), 7.01(t, 1H), 7.17(s, 1H), 7.20–7.30(m, 2H), 7.73(s, 1H), 7.81(d, 1H), 7.90(s, 1H), 8.38(d, 1H), 10.42(s, 1H).<br><br>Analysis: Found: C, 55.83; H, 4.24; N, 6.44. $C_{21}H_{18}N_2O_4S_2$ Requires: C, 59.13; H, 4.25; N, 6.57. |
| 34 | 2-Me-C₆H₄-S(O)-Me (structure) | Et | m.p. 140–142° C. (from diethyl ether)<br>LRMS(Thermospray): 425.3(MH⁺)<br>$^1$H NMR(300 MHz, CDCl$_3$): δ = 1.39(t, 3H), 2.50(s, 3H), 4.38(m, 2H), 5.23(s, 2H), 6.92(s, 1H), 7.12(s, 1H), 7.17–7.37(m, 4H), 7.53(s, 1H), 7.58(s, 1H), 7.85 (d, 1H), 8.70(d, 1H).<br>$C_{22}H_{20}N_2O_3S_2$ |

Example 35

Ethyl 3-(2-[(methylcarbonyloxy)methyl]phenylsulfinyl)-6-(3-pyridylmethoxy)benzo[b]thiophene-2-carboxylate

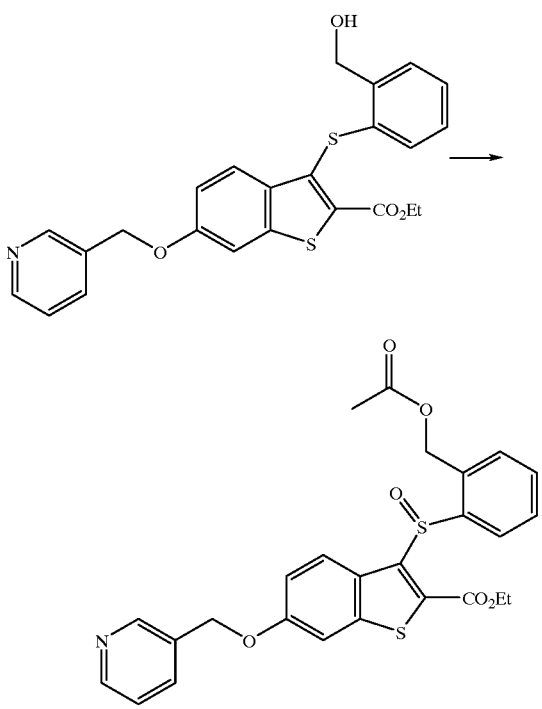

Hydrogen peroxide in water (0.23 ml of 30% w/v, 2.05 mmol) was added to a mixture of ethyl 3-[2-(hydroxymethyl)phenylsulfanyl]-6-(3-pyridylmethoxy)benzo[b]thiophene-2-carboxylate (Example 13, 770 mg, 1.71 mmol) in acetic acid (5 ml), and 2M aqueous hydrochloric acid (0.8 ml). The mixture was heated to 100° C. for 3 hours, cooled, and the solvents removed under reduced pressure. The residue was partitioned between ethyl acetate and aqueous sodium bicarbonate solution, and the organic layer was separated, dried (magnesium sulfate) and concentrated under vacuo. The residue was flash chromatographed on silica gel using a mixture of 75% ethyl acetate and 25% hexane as eluant, to give the title compound as a colourless solid (500 mg).

LRMS (Thermospray): 510.2 (MH$^+$)

$^1$H NMR (400 MHz, CDCl$_3$): δ=1.38 (t, 3H), 2.04 (s, 3H), 4.38 (m, 2H), 5.15 (s, 2H), [5.27 (d, 1H) & 5.60 (d, 1H) non-equivalent C$\underline{H}_2$OAc], 7.10 (d, 1H), 7.35 (m, 2H), 7.45 (m, 3H), 7.79 (d, 1H), 7.97 (dd, 1H), 8.61 (d, 1H), 8.70 (s, 1H), 8.78 (d, 1H). C$_{26}$H$_{23}$NO$_6$S$_2$

Example 36

Ethyl 3-[(3-methoxyphenyl)sulfinyl]-6-[(3-pyridyloxy)methyl]benzo[b]thiophene-2-carboxylate

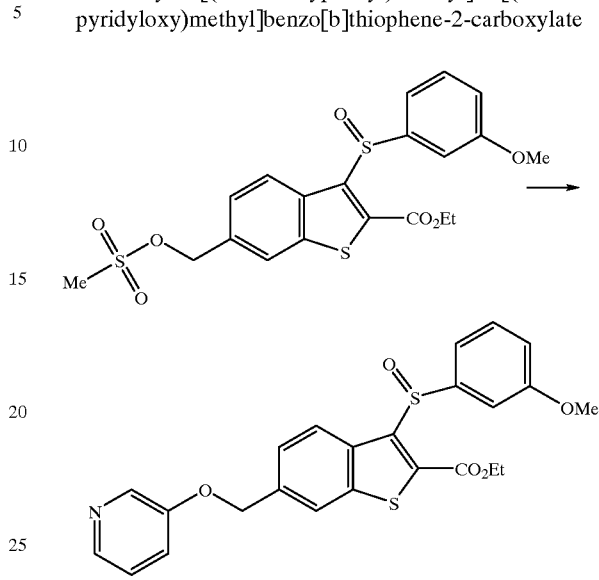

3-Hydroxypyridine (57 mg, 0.6 mmol) was added to a stirred suspension of sodium hydride (24 mg of 60% dispersion in mineral oil, 0.6 mmol) in anhydrous dimethylformamide (2 ml), under a nitrogen atmosphere. After 30 minutes, ethyl 3-[(3-methoxyphenyl)sulfinyl]-6-[(methylsulfonyloxy)methyl]benzo[b]thiophene-2-carboxylate (Preparation 18, 234 mg, 0.5 mmol) was added to the mixture, and the mixture was stirred for 3 hours. The reaction was partitioned between ethyl acetate and water. The organics were separated and washed with water, dried (magnesium sulfate) and evaporated under reduced pressure. The residue was flash chromatographed on silica gel using 2% ethanol in dichloromethane as eluant The semi-pure product was re-chromatographed on silica gel using ethyl acetate, and then crystallised from diethyl ether, to give the title compound as a colourless solid (110 mg).

m.p. 113–115° C. (from diethyl ether)

LRMS (Thermospray): 468.3 (MH$^+$) for C$_{24}$H$_{21}$NO$_5$S$_2$ $^1$H NMR (300 MHz, CDCl$_3$): δ=1.47 (t, 3H), 3.81 (s, 3H), 4.50 (q, 2H), 5.20 (s, 2H), 6.92 (d, 1H), 7.17–7.27 (m, 2H), 7.33 (t, 1H), 7.39–7.47 (m, 2H), 7.51 (s, 1H), 7.90 (s, 1H), 8.24 (d, 1H), 8.40 (s, 1H), 8.80 (d, 1H).

Examples 37–38

These were prepared by the method of Example 36, using 3,4-(methylenedioxy)phenol for Example 37, and 1,2,4-triazole for Example 38, in place of 3-hydroxypyridine. Their physical data are shown in Table 6.

TABLE 6

| Example N° | Y—R² | Physical Data |
|---|---|---|
| 37 | (methylenedioxyphenyl-O-CH₂–) | m.p. 133–135° C. (from diethyl ether and hexane)<br>LRMS(APCI): 511.1(MH⁺)<br>¹H NMR(300 MHz, CDCl₃): δ = 1.44(t, 3H), 3.82(s, 3H), 4.49 (q, 2H), 5.07(s, 2H), 5,92(s, 2H), 6.38(dd, 1H), 6.55(s, 1H), 6.69(d, 1H), 6.92(dd, 1H), 7.30–7.45(m, 3H), 7.52(s, 1H), 7.90 (s, 1H), 8.75(d, 1H).<br><br>Analysis: Found: C, 61.67; H, 4.74; N, 0.00.<br>$C_{26}H_{22}O_7S_2$ Requires: C, 61.16; H, 4.34; N, 0.00. |
| 38 | (1,2,4-triazol-1-yl-CH₂–) | m.p. 148–149° C. (from diethyl ether)<br>LRMS(Thermospray): 442.0(MH⁺)<br>¹H NMR(300 MHz, CDCl₃): δ = 1.43(t, 3H), 3.80(s, 3H), 4.50 (q, 2H), 5.42(s, 2H), 6.92(d, 1H), 7.23–7.40(m, 3H), 7.47(s, 1H), 7.68(s, 1H), 7.98(s, 1H), 8.10(s, 1H), 8.77(d, 1H).<br><br>Analysis: Found: C, 56.66; H, 4.24; N, 9.20.<br>$C_{21}H_{19}N_3O_4S_2$ Requires: C, 57.12; H, 4.34; N, 9.52. |

Example 39

Ethyl 3-[(3-methoxyphenyl)sulfinyl]-6-(4-pyridylmethoxy)benzo[b]thiophene-2-carboxylate

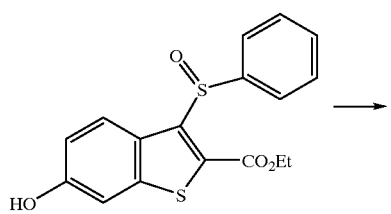

→

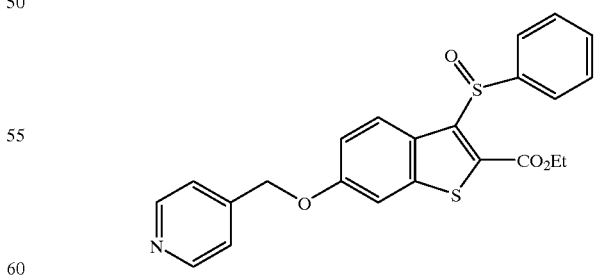

Potassium carbonate (240 mg, 1.73 mmol) was added to a solution of ethyl 6-hydroxy-3-(phenylsulfinyl)benzo[b]thiophene-2-carboxylate (Preparation 19, 200 mg, 0.58 mmol) in anhydrous dimethylformamide (3 ml) at ambient temperature under a nitrogen atmosphere. After 15 minutes 4-(chloromethyl)pyridine hydrochloride (104 mg, 0.64 mmol) was added, and stirring continued for 24 hours. The mixture was partitioned between ethyl acetate and water, and the organic layer was separated and washed twice with water, dried (magnesium sulfate), and evaporated under reduced pressure. The residue was purified by flash chromatography on silica gel using ethyl acetate as eluant, and crystallised from diisopropyl ether to give the title compound as a colourless solid (198 mg).

m.p. 153–155° C.

LRMS (Thermospray): 438.2 (MH$^+$)

Analysis: Found: C, 62.96; H, 4.36; N, 3.10. $C_{23}H_{19}NO_4S_2$ Requires: C, 63.14; H, 4.38; N, 3.20.

$^1$H NMR (300 MHz, CDCl$_3$): δ=1.43 (t, 3H), 4.46 (q, 2H), 5.15 (s, 2H), 7.07 (dd, 1H), 7.26 (s, 1H), 7.33 (d, 2H), 7.40–7.50 (m, 3H), 7.90 (d, 2H), 8.62 (d, 2H), 8.73 (d, 1H).

Examples 40–51

These were prepared following the method of Example 39, by reacting the appropriate alkylating agents such as R$^2$—CH$_2$—Cl, and R$^2$—CH(CH$_3$)—Cl, with the intermediate from Preparation 19. These alkylating agents are either commercially available or prepared as described in the chemical literature.

Their physical data are shown in Table 7.

TABLE 7

| Example N° | Y / R$^2$ | Physical Data |
|---|---|---|
| 40 | (pyridin-2-yl)methoxy | LRMS(Thermospray): 437.9(MH$^+$)<br>$^1$H NMR(400 MHz, CDCl$_3$): δ = 1.42(t, 3H), 4.43(q, 2H), 5.22 (s, 2H), 7.09(d, 1H), 7.22(dd, 1H), 7.30(s, 1H), 7.37–7.50(m, 4H), 7.70(dd, 1H), 7.90(d, 2H), 8.59(d, 1H), 8.70(d, 1H).<br>$C_{23}H_{19}NO_4S_2$. |
| 41 | (6-methoxypyridin-3-yl)methoxy | m.p. 123–125° C. (from diisopropyl ether)<br>$^1$H NMR(300 MHz, CDCl$_3$): δ = 1.44(t, 3H), 3.95(s, 3H), 4.45 (q, 2H), 5.02(s, 2H), 6.78(d, 1H), 7.04(dd, 1H), 7.29(s, 1H), 7.40–7.49(m, 3H), 7.63(dd, 1H), 7.90(d, 2H), 8.20(s, 1H), 8.70 (d, 1H).<br><br>Analysis: Found: C, 61.38; H, 4.52; N, 3.01.<br>$C_{24}H_{21}NO_5S_2$ Requires: C, 61.65; H, 4.53; N, 3.00. |
| 42 | 1-(pyridin-3-yl)ethoxy | mixture of diastereoisomers<br>LRMS(Thermospray): 452.4(MH$^+$).<br>$^1$H NMR(300 MHz, CDCl$_3$): δ = 1.39(t, 3H), 1.65(pair of d, 3H), 4.40(m, 2H), 5.37(q, 1H), 6.97(d, 1H), 7.10(d, 1H), 7.24 (m, 1H), 7.33–7.44(m, 3H), 7.65(m, 1H), 7.83(d, 2H), 8.50(m, 1H), 8.60(m, 2H).<br>$C_{24}H_{21}NO_4S_2$ |

TABLE 7-continued

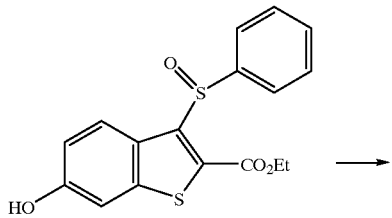

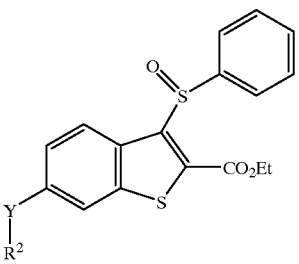

| Example N° | Y / R² | Physical Data |
|---|---|---|
| 43 | 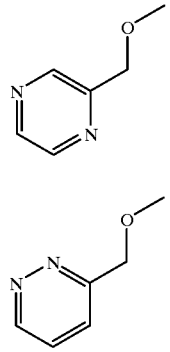 | LRMS(Thermospray): 439.8(MH⁺).<br>$^1$H NMR(400 MHz, CDCl$_3$): δ = 1.40(t, 3H), 4.40(m, 2H), 5.23 (s, 2H), 7.07(d, 1H), 7.30(s, 1H), 7.36–7.43(m, 3H), 7.83(d, 2H), 8.53(s, 1H), 8.54(s, 1H), 8.67(d, 1H), 8.77(s, 1H).<br>$C_{22}H_{18}N_2O_4S_2$. |
| 44 | 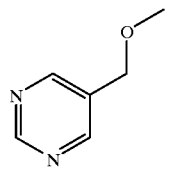 | LRMS(Thermospray): 439.7(MH⁺).<br>$^1$H NMR(400 MHz, CDCl$_3$): δ = 1.40(t, 3H), 4.40(m, 2H), 5.43 (s, 2H), 7.05(d, 1H), 7.28–7.50(m, 5H), 7.65(d, 1H), 7.83(d, 2H), 8.66(d, 1H), 9.10(s, 1H).<br>$C_{22}H_{18}N_2O_4S_2$. |
| 45 | 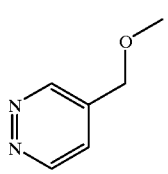 | m.p. 155° C. (from diisopropyl ether)<br>LRMS(APCI): 439.5(MH⁺).<br>$^1$H NMR(400 MHz, CDCl$_3$): δ = 1.40(t, 3H), 4.42(m, 2H), 5.08 (s, 2H), 7.03(d, 1H), 7.27(s, 1H), 7.35–7.45(m, 3H), 7.86(d, 2H), 8.70(d, 1H), 8.80(s, 2H), 9.20(s, 1H).<br>$C_{22}H_{18}N_2O_4S_2$. |
| 46 | 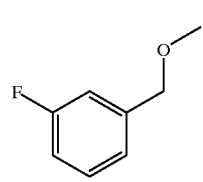 | LRMS(Thermospray): 439.4(MH⁺).<br>$^1$HNMR(400 MHz, DMSO-d$_6$): δ = 1.36(t, 3H), 4.41(q, 2H), 5.30(s, 2H), 7.20(d, 1H), 7.44–7.58(m, 3H), 7.70(d, 1H), 7.80 (m, 3H), 8.53(d, 1H), 9.21(d, 1H), 9.32(s, 1H).<br><br>Analysis: Found: C, 59.73; H, 4.11; N, 6.26.<br>$C_{22}H_{18}N_2O_4S_2$; Requires: C, 60.26; H, 4.14; N, 6.39. |
| 47 | (3-fluorobenzyl OMe structure) | m.p. 149–151° C. (from diisopropyl ether)<br>LRMS(Thermospray): 455.0(MH⁺).<br>$^1$H NMR(300 MHz, CDCl$_3$): δ = 1.43(t, 3H), 4.46(q, 2H), 5.11 (s, 2H), 7.00–7.50(m, 9H), 7.90(d, 2H), 8.70(d, 1H).<br><br>Analysis: Found: C, 63.43; H, 4.16. |

TABLE 7-continued

| Example N° | Y–R² | Physical Data |
|---|---|---|
| | | $C_{24}H_{19}FO_4S_2$; Requires: C, 63.42; H, 4.21. |
| 48 | (benzo[1,3]dioxol-5-ylmethoxy)methyl | LRMS(Thermospray): 480.9(MH⁺).<br>¹H NMR(400 MHz, CDCl₃): δ = 1.42(t, 3H), 4.45(m, 2H), 5.00 (s, 2H), 5.98(s, 2H), 6.79–6.83(m, 3H), 7.04(d, 1H), 7.30(s, 1H), 7.40–7.53(m, 3H), 7.89(d, 2H), 8.68(d, 1H).<br>$C_{25}H_{20}O_6S_2$ |
| 49 | (3-cyanobenzyl)oxymethyl | m.p. 175–177° C. (from diisopropyl ether)<br>LRMS(Thermospray): 462.0(MH⁺).<br>¹H NMR(300 MHz, CDCl₃): δ = 1.43(t, 3H), 4.46(q, 2H), 5.15 (s, 2H), 7.06(dd, 1H), 7.28(1H, obscured by CDCl₃), 7.40–7.53 (m, 4H), 7.65(m, 2H), 7.73(s, 1H), 7.90(d, 2H), 8.73(d, 1H).<br><br>Analysis: Found: C, 64.65, H, 4.08; N, 3.06.<br>$C_{25}H_{19}NO_4S_2$; Requires: C, 65.05; H, 4.15; N, 3.04. |
| 50 | (thiophen-3-ylmethoxy)methyl | m.p. 127° C. (from diisopropyl ether)<br>LRMS(Thermospray): 443.0(MH⁺).<br>¹H NMR(300 MHz, CDCl₃): δ = 1.43(t, 3H), 4.44(q, 2H), 5.13 (s, 2H), 7.05(dd, 1H), 7.13(d, 1H), 7.23–7.50(m, 6H), 7.80(d, 2H), 8.68(d, 1H).<br>$C_{22}H_{18}O_4S_3$ |
| 51 | (thiazol-5-ylmethoxy)methyl | m.p. 142° C. (from diisopropyl ether)<br>LRMS(Thermospray): 444.3(MH⁺).<br>¹H NMR(400 MHz, CDCl₃): δ = 1.43(t, 3H), 4.43(m, 2H), 5.34 (s, 2H), 7.05(dd, 1H), 7.33(s, 1H), 7.40–7.50(m, 3H), 7.85–7.95 (m, 3H), 8.70(d, 1H), 8.83(s, 1H).<br>$C_{21}H_{17}NO_4S_3$. |

Example 52

3-(Phenylsulfanyl)-6-(3-pyridylmethoxy)benzo[b]thiophene-2-carboxylic Acid

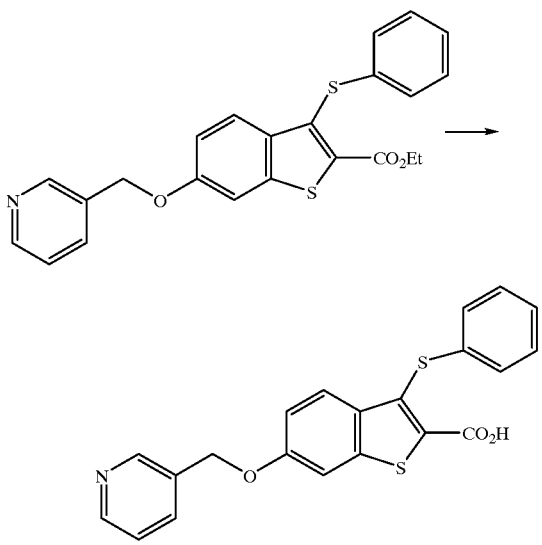

Sodium hydroxide (0.5 ml of 2M in water) was added to a solution of ethyl 3-(phenylsulfanyl)-6-(3-pyridylmethoxy)benzo[b]thiophene-2-carboxylate (Example 1, 190 mg, 0.45 mmol) in 1,4-dioxane, and the mixture heated to 60° C. for 4 hours. The solvents were removed under reduced pressure, and the residue was dissolved in water (15 ml) and washed with ethyl acetate (25 ml). The aqueous layer was separated and acidified by dropwise addition of acetic acid until a white solid precipitated. The solid was isolated by filtration and dried under vacuo to give the title compound as a colourless solid (140 mg).

m.p. 236–238° C.

$^1$H NMR (300 MHz, DMSO-d$_6$): δ=5.20 (s, 2H), 7.04–7.28 (m, 6H), 7.40 (dd, 1H), 7.55 (d, 1H), 7.78 (d, 1H), 7.88 (d, 1H), 8.53 (d, 1H), 8.66 (s, 1H), 13.5 (brs, 1H).

Analysis: Found: C, 63.89; H, 3.82; N, 3.46. C$_{21}$H$_{15}$NO$_3$S$_2$ Requires: C, 64.10; H, 3.84; N, 3.56.

Examples 53–95

These were prepared by the method of Example 52, using the appropriate substituted benzo[b]thiophene-2-carboxylate esters as described earlier. Some of the Examples used methanol in place of, or in addition to, 1,4-dioxane as solvent. Their physical data are shown in Tables 8, 9, 10, 11, 12 and 13.

TABLE 8

| Example N° | X—R$^1$ | Physical Data |
|---|---|---|
| 53 | S-benzo[1,3]dioxole | m.p. 226–228° C.<br>LRMS(APCI): 437.8(MH$^+$)<br>$^1$H NMR(300 MHz, DMSO-d$_6$): δ = 5.22(s, 2H), 5.97(s, 2H), 6.80 (m, 3H), 7.10(dd, 1H), 7.40(dd, 1H), 7.62(d, 1H), 7.72(s, 1H), 7.86 (d, 1H), 8.54(d, 1H), 8.67(s, 1H).<br>C$_{22}$H$_{15}$NO$_5$S$_2$. |
| 54 | S-(3-methoxyphenyl) | m.p. 210–214° C.<br>LRMS(APCI): 380.2(MH$^+$-CO$_2$), 423.7(MH$^+$)<br>$^1$H NMR(300 MHz, DMSO-d$_6$): δ = 3.64(s, 3H), 5.21(s, 2H), 6.60 (d, 1H), 6.66(s, 1H), 6.72(d, 1H), 7.07–7.18(m, 2H), 7.40(dd, 1H), 7.56(d, 1H), 7.78(s, 1H), 7.88(d, 1H), 8.53(d, 1H), 8.67(s, 1H).<br><br>Analysis: Found: C, 61.49; H, 3.94; N, 3.32.<br>C$_{22}$H$_{17}$NO$_4$S$_2$; 1/4 H$_2$O  Requires: C, 61.74; H, 4.12; N, 3.27. |
| 55 | S-(2-methylphenyl) | m.p. 250–251° C.<br>$^1$H NMR(300 MHz, DMSO-d$_6$): δ = 2.38(s, 3H), 5.20(s, 2H), 6.70 (d, 1H), 6.93–7.13(m, 3H), 7.21(d, 1H), 7.39–7.45(m, 2H), 7.78(s, 1H), 7.88(d, 1H), 8.54(d, 1H), 8.67(s, 1H). |

TABLE 8-continued

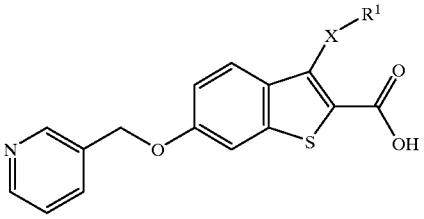

| Example N° | X-R¹ | Physical Data |
|---|---|---|
| | | Analysis:     Found:    C, 64.26; H, 4.24; N, 3.41.<br>C₂₂H₁₇NO₃S₂; 1/5 H₂O    Requires:   C, 64.28; H, 4.27; N, 3.41. |
| 56 | 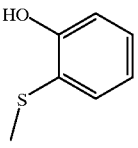 | m.p. 261–263° C.<br>LRMS(APCI): 366.1(MH⁺–CO₂), 409.7(MH⁺)<br>¹H NMR(300 MHz, DMSO-d₆): δ = 5.19(s, 2H), 6.60(m, 2H), 6.80 (d, 1H), 6.92–7.08(m, 2H), 7.42(dd, 1H), 7.52(d, 1H), 7.73(s, 1H), 7.87(d, 1H), 8.55(d, 1H), 8.67(s, 1H). |
| | | Analysis:     Found:    C, 60.05; H, 3.65; N, 3.27.<br>C₂₁H₁₅NO₄S₂; 1/2 H₂O    Requires:   C, 60.27; H, 3.85; N, 3.35. |
| 57 | 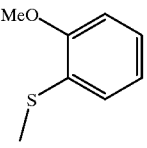 | m.p. 215–216° C.<br>LRMS(Thermospray): 379.7(MH⁺–CO₂), 423.6(MH⁺)<br>¹H NMR(300 MHz, DMSO-d₆): δ = 3.85(s, 3H), 5.22(s, 2H), 6.46 (d, 1H), 6.71(dd, 1H), 7.00(d, 1H), 7.05–7.15(m, 2H), 7.41(dd, 1H), 7.50(d, 1H), 7.79(s, 1H), 7.88(d, 1H), 8.55(d, 1H), 7.68(s, 1H), 13.5(brs, 1H). |
| | | Analysis:     Found:    C, 60.70; H, 4.35; N, 3.03.<br>C₂₂H₁₇NO₄S₂; 1/2 H₂O    Requires:   C, 61.09; H, 4.20; N, 3.24. |
| 58 | 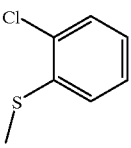 | m.p. 220–222° C.<br>LRMS(Thermospray): 384.3(MH⁺–CO₂), 428.0(MH⁺)<br>¹H NMR(300 MHz, DMSO-d₆): δ = 5.22(s, 2H), 6.58(d, 1H), 7.05– 7.18(m, 3H), 7.40–7.56(m, 3H), 7.82(s, 1H), 7.90(d, 1H), 8.54(d, 1H), 8.69(s, 1H), 13.53(brs, 1H). |
| | | Analysis:     Found:    C, 58.41; H, 3.33; N, 3.26.<br>C₂₁H₁₄ClNO₃S₂         Requires:   C, 58.94; H, 3.30; N, 3.27. |
| 59 | 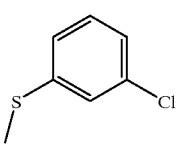 | m.p. 237–238° C.<br>LRMS(Thermospray): 384.3(MH⁺–CO₂), 428.0(MH⁺)<br>¹H NMR(300 MHz, DMSO-d₆): δ = 5.22(s, 2H), 7.00(d, 1H), 7.10– 7.30(m, 4H), 7.40(dd, 1H), 7.60(d, 1H), 7.80(s, 1H), 7.89(d, 1H), 8.54(d, 1H), 8.68(s, 1H), 13.65(brs, 1H). |
| | | Analysis:     Found:    C, 58.54; H, 3.38; N, 3.08.<br>C₂₁H₁₄ClNO₃S₂         Requires:   C, 58.94; H, 3.30; N, 3.27. |
| 60 | 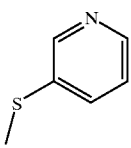 | m.p. 227–229° C.<br>LRMS(Thermospray): 351.3(MH⁺–CO₂), 395.0(MH⁺)<br>¹H NMR(300 MHz, DMSO-d₆): δ = 5.22(s, 2H), 7.13(d, 1H), 7.26 (dd, 1H), 7.40–7.50(m, 2H), 7.62(d, 1H), 7.81(s, 1H), 7.90(d, 1H), 8.36(d, 1H), 8.39(s, 1H), 8.55(d, 1H), 8.70(s, 1H), 13.70(brs, 1H).<br>C₂₀H₁₄N₂O₃S₂ |

TABLE 8-continued

| Example No | X-R¹ | Physical Data |
|---|---|---|
| 61 | 2-F-C₆H₄-S- | m.p. 241–242° C.<br>¹H NMR(400 MHz, DMSO-d₆): δ = 5.19(s, 2H), 6.84(dd, 1H), 7.00 (m, 1H), 7.08(dd, 1H), 7.16–7.23(m, 2H), 7.38(m, 1H), 7.52(d, 1H), 7.76(s, 1H), 7.84(d, 1H), 8.50(d, 1H), 8.65(s, 1H).<br>$C_{21}H_{14}FNO_3S_2$ |
| 62 | 2-(HOCH₂)-C₆H₄-S- | m.p. 248° C.<br>LRMS(Thermospray): 380.2(MH⁺-CO₂), 424.3(MH⁺).<br>¹H NMR(400 MHz, DMSO-d₆): δ = 4.65(s, 2H), 5.21(s, 2H), 5.35 (brs, 1H), 6.76(d, 1H), 7.05(m, 2H), 7.18(t, 1H), 7.40–7.50(m, 3H), 7.76(s, 1H), 7.88(d, 1H), 8.55(d, 1H), 8.68(s, 1H).<br>$C_{22}H_{17}NO_4S_2$ |
| 63 | C₆H₅-S(O)₂- | m.p. 218–220° C.<br>LRMS(Thermospray): 381.8(MH⁺–CO₂).<br>¹H NMR(300 MHz, DMSO-d₆): δ = 5.21(s, 2H), 7.28(d, 1H), 7.42 (dd, 1H), 7.58–7.73(m, 3H), 7.80–7.92(m, 2H), 8.13(d, 2H), 8.27(d, 1H), 8.56(d, 1H), 8.68(s, 1H), 14.4(brs, 1H).<br><br>Analysis: Found: C, 59.26; H, 3.57; N, 3.18.<br>$C_{21}H_{15}NO_5S_2$ Requires: C, 59.28; H, 3.55; N, 3.29. |
| 64 | C₆H₅-S(O)- | m.p. 260–263° C.<br>LRMS(Thermospray): 366.1(MH⁺-CO₂).<br>¹H NMR(300 MHz, DMSO-d₆): δ = 5.20(s, 2H), 7.10(d, 1H), 7.38–7.57(m, 4H), 7.70–7.80(m, 3H), 7.86(d, 1H), 8.47(d, 1H), 8.53(d, 1H), 8.66(s, 1H), 14.2(brs, 1H).<br><br>Analysis: Found: C, 61.27; H, 3.64; N, 3.34.<br>$C_{21}H_{15}NO_4S_2$ Requires: C, 61.59; H, 3.69; N, 3.42. |
| 65 | 3-MeO-C₆H₄-S(O)- | m.p. 239–241° C.<br>LRMS(Thermospray): 396.2(MH⁺-CO₂)<br>¹H NMR(300 MHz, DMSO-d₆): δ = 3.75(s, 3H), 5.20(s, 2H), 7.00 (dd, 1H), 7.13(dd, 1H), 7.25–7.45(m, 4H), 7.78(s, 1H), 7.86(d, 1H), 8.49(d, 1H), 8.53(d, 1H), 8.66(s, 1H).<br><br>Analysis: Found: C, 59.44; H, 3.83; N, 3.06.<br>$C_{22}H_{17}NO_5S_2$ Requires: C, 60.44; H, 3.90; N, 3.19. |
| 66 | 3-F-C₆H₄-S(O)- | m.p. 156° C.<br>LRMS(Thermospray): 384.2(MH⁺-CO₂).<br>¹H NMR(400 MHz, DMSO-d₆): δ = 5.18(s, 2H), 7.10(d, 1H), 7.27 (dd, 1H), 7.38(m, 1H), 7.50–7.60(m, 3H), 7.76(s, 1H), 7.82(d, 1H), 8.40(d, 1H), 8.50(d, 1H), 8.63(s, 1H).<br>$C_{21}H_{14}FNO_4S_2$. |

TABLE 8-continued

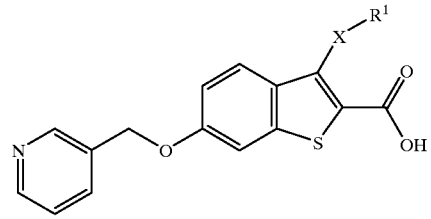

| Example N° | X-R¹ | Physical Data |
|---|---|---|
| 67 | 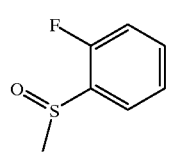 | m.p. 238° C.<br>LRMS(Thermospray): 384.2(MH⁺-CO₂).<br>¹H NMR(400 MHz, DMSO-d₆): δ = 5.18(s, 2H), 7.08(dd, 1H), 7.21 (dd, 1H), 7.33–7.40(m, 2H), 7.50(m, 1H), 7.72–7.85(m, 3H), 8.34 (d, 1H), 8.50(d, 1H), 8.63(s, 1H).<br>$C_{21}H_{14}FNO_4S_2$. |
| 68 | 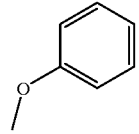 | m.p. 248–250° C.<br>LRMS(Thermospray): 333.8(MH⁺-CO₂), 378.2(MH⁺).<br>¹H NMR(300 MHz, DMSO-d₆): δ = 5.23(s, 2H), 6.90(d, 2H), 7.00–7.13(m, 2H), 7.23–7.46(m, 4H), 7.76(s, 1H), 7.90(d, 1H), 8.55(d, 1H), 8.70(s, 1H), 13.2(brs, 1H).<br>$C_{21}H_{15}NO_4S$ |

TABLE 9

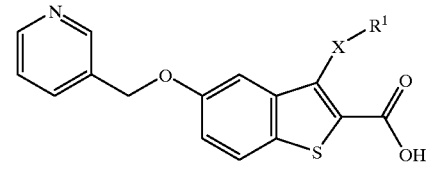

| Example N° | X-R¹ | Physical Data |
|---|---|---|
| 69 | 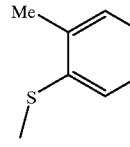 | m.p. 235° C.<br>LRMS(Thermospray): 364.1(MH⁺-CO₂)<br>¹H NMR(400 MHz, DMSO-d₆): δ = 2.39(s, 3H), 4.94(s, 2H), 6.70 (d, 1H), 6.90–7.06(m, 3H), 7.13(d, 1H), 7.19(d, 1H), 7.36(dd, 1H), 7.72(d, 1H), 7.85(d, 1H), 8.50(d, 1H), 8.56(s, 1H).<br>$C_{22}H_{17}NO_3S_2$ |
| 70 | 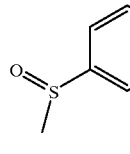 | m.p. 245° C.<br>LRMS(Thermospray): 366.1(MH⁺-CO₂)<br>¹H NMR(400 MHz, DMSO-d₆): δ = [5.08(d, 1H), 5.09(d, 1H) non-equivalent OC$\underline{H}_2$Py₃], 7.28(d, 1H), 7.40–7.55(m, 4H), 7.78(d, 2H), 7.88(d, 1H), 8.00(d, 1H), 8.15(s, 1H), 8.56(d, 1H), 3.69(s, 1H). |

| | Analysis: | Found: | C, 59.88; H, 3.49; N, 3.23. |
|---|---|---|---|
| | $C_{21}H_{15}NO_4S_2$; 1/2 H₂O | Requires: | C, 60.27; H, 3.85; N, 3.35. |

TABLE 10

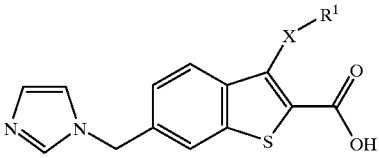

| Example N° | X–R¹ | Physical Data |
|---|---|---|
| 71 | 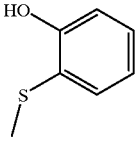 | m.p. 168–170° C.<br>LRMS(Thermospray): 339.6(MH⁺-CO₂), 383.3(MH⁺)<br>¹H NMR(300 MHz, DMSO-d₆): δ = 5.33(s, 2H), 6.60(t, 1H), 6.74(d, 1H), 6.95–7.05(m, 2H), 7.15(s, 1H), 7.30(d, 1H), 7.39(s, 1H), 7.77 (d, 1H), 7.90(s, 1H), 8.25(s, 1H).<br><br>Analysis:    Found:    C, 57.27; H, 3.77; N, 7.00.<br>C₁₉H₁₄N₂O₃S₂; H₂O    Requires:    C, 56.98; H, 4.03; N, 6.99. |
| 72 | 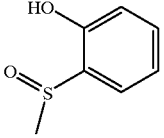 | m.p. 235–238° C.<br>HRMS(+ve ion electrospray): 399.0(MH⁺)<br>¹H NMR(300 MHz, DMSO-d₆ + drop TFA-d): δ = 5.51(s, 2H), 6.73 (d, 1H), 6.99(t, 1H), 7.22(t, 1H), 7.36(d, 1H), 7.62(s, 1H), 7.74(s, 1H), 7.82(d, 1H), 8.03(s, 1H), 8.36(d, 1H), 9.22(s, 1H).<br><br>Analysis:    Found:    C, 55.99; H, 3.56; N, 6.76.<br>C₁₉H₁₄NO₄S₂; 1/2 H₂O;    Requires:    C, 56.00; H, 3.71; N, 6.88. |
| 73 | 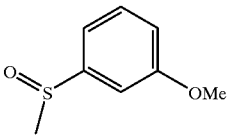 | LRMS(Thermospray): 369.2(MH⁺-CO₂).<br>¹H NMR(300 MHz, DMSO-d₆ + drop TFA-d): δ = 3.73(s, 3H), 5.53(s, 2H), 6.99(d, 1H), 7.28–7.48(m, 4H), 7.65(s, 1H), 7.75(s, 1H), 8.08(s, 1H), 8.60(d, 1H), 9.22(s, 1H).<br><br>Analysis:    Found:    C, 57.05; H, 3.80; N, 6.61.<br>C₂₀H₁₆N₂O₄S₂; 1/2 H₂O    Requires:    C, 56.99; H, 4.06; N, 6.65. |
| 74 | 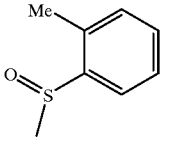 | m.p. 224–226° C.<br>LRMS(Thermospray): 353.3(MH⁺-CO₂).<br>¹H NMR(300 MHz, DMSO-d₆ + drop TFA-d): δ = 2.33(s, 3H), 5.53(s, 2H), 7.21(m, 1H), 7.30–7.43(m, 3H), 7.63(s, 1H), 7.75(s, 1H), 7.81 (dd, 1H), 8.10(s, 1H), 8.52(d, 1H), 9.22(s, 1H).<br><br>Analysis:    Found:    C, 59.68; H, 4.00; N, 6.87.<br>C₂₀H₁₆N₂O₃S₂; 1/4 H₂O    Requires:    C, 59.90; H, 4.14; N, 6.99. |

TABLE 11
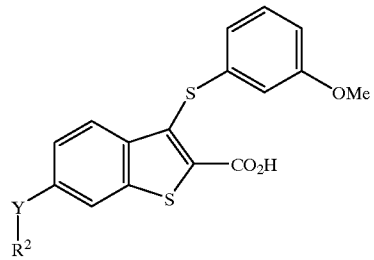
| Example Nº | Y/R² | Physical Data |
|---|---|---|
| 75 | 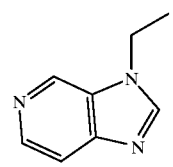 | m.p. >270° C.<br>LRMS(APCI): 404.2(MH⁺-CO₂).<br>¹H NMR(300 MHz, DMSO-d₆): δ = 3.62(s, 3H), 5.72(s, 2H), 6.59(d, 1H), 6.67(s, 1H), 6.70(d, 1H), 7.10(t, 1H), 7.40(d, 1H), 7.63–7.70(m, 2H), 8.13(s, 1H), 8.30(d, 1H), 8.63(s, 1H), 8.92 (s, 1H).<br>$C_{23}H_{17}N_3O_3S_3$ |
| 76 | 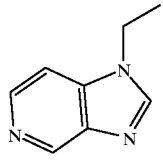 | m.p. 160–162° C.<br>LRMS(APCI): 404.2(MH⁺-CO₂).<br>¹H NMR(300 MHz, DMSO-d₆): δ = 3.61(s, 3H), 5.63(s, 2H), 6.58(d, 1H), 6.65(s, 1H), 6.69(d, 1H), 7.10(t, 1H), 7.34(d, 1H), 7.59–7.65(m, 2H), 8.02(s, 1H), 8.29(d, 1H), 8.57(s, 1H), 8.93 (s, 1H).<br>$C_{23}H_{17}N_3O_3S_2$ |
TABLE 12
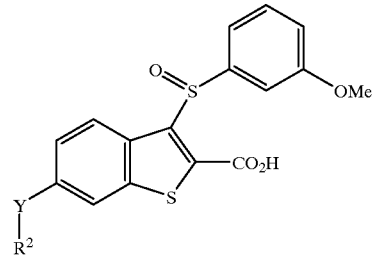
| Example Nº | Y/R² | Physical Data |
|---|---|---|
| 77 | 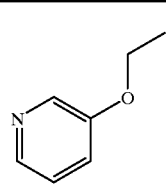 | m.p. 224–226° C.<br>LRMS(Thermospray): 396.3(MH⁺-CO₂).<br>¹H NMR(300 MHz, DMSO-d₆): δ = 3.77(s, 3H), 5.28(s, 2H), 7.01(dd, 1H), 7.27–7.55(m, 6H), 8.15–8.20(m, 2H), 8.36(d, 1H), 8.60(d, 1H).<br>$C_{22}H_{17}NO_5S_2$ |

TABLE 12-continued

| Example N° | Y / R² | Physical Data |
|---|---|---|
| 78 | 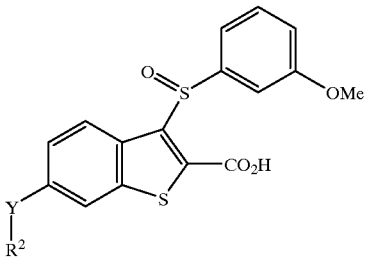 | m.p. 85–88° C.<br>LRMS(Thermospray): 439.1(MH⁺-CO₂), 482.6(MH⁺).<br>$^1$H NMR(300 MHz, DMSO-d$_6$): δ = 3.77(s, 3H), 5.10(s, 2H), 5.93(s, 2H), 6.42(dd, 1H), 6.70(s, 1H), 6.78(d, 1H), 7.02(d, 1H), 7.30–7.52(m, 4H), 8.15(s, 1H), 8.58(d, 1H), 14.5(brs, 1H).<br><br>Analysis:  Found:    C, 58.39; H, 3.66; N, nil.<br>$C_{24}H_{18}O_7S_2$; 1/2 H₂O   Requires: C. 58.64; H, 3.90; N, nil. |
| 79 | 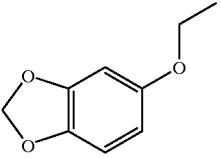 | m.p. 249–251° C.<br>LRMS(Thermospray): 370.0(MH⁺-CO₂).<br>$^1$H NMR(300 MHz, DMSO-d$_6$): δ = 3.77(s, 3H), 5.50(s, 2H), 7.00(d, 1H), 7.30–7.45(m, 4H), 7.92(s, 1H), 7.98(s, 1H), 8.55 (d, 1H), 8.62(s, 1H).<br><br>Analysis:  Found:    C, 54.79; H, 3.28; N, 9.93.<br>$C_{19}H_{15}N_3O_4S_2$;   Requires: C, 55.19; H, 3.66; N, 10.17. |

TABLE 13

| Example N° | Y / R² | Physical Data |
|---|---|---|
| 80 | 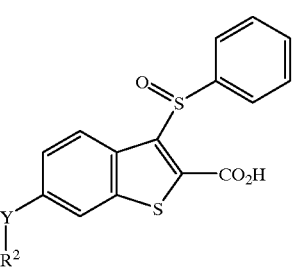 | m.p. 206–208° C.(recrystallised from diethyl ether)<br>LRMS(Thermospray): 365.0(MH⁺-CO₂).<br>$^1$H NMR(300 MHz, DMSO-d$_6$): δ = 5.16(s, 2H), 7.10(d, 1H), 7.28–7.60(m, 8H), 7.70–7.88(m, 3H), 8.48(d, 1H).<br><br>Analysis:  Found:    C, 64.08; H, 3.88; N, nil.<br>$C_{22}H_{16}O_4S_2$;   Requires: C, 64.68; H, 3.95; N, nil. |

TABLE 13-continued

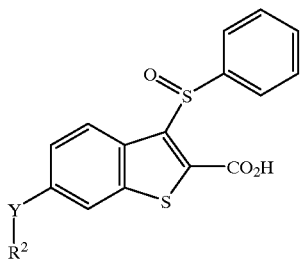

| Example N° | Y / R² | Physical Data |
|---|---|---|
| 81 | 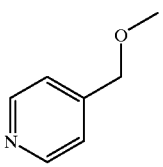 | m.p. >260° C.<br>LRMS(Thermospray): 366.1(MH$^+$-CO$_2$).<br>$^1$H NMR(300 MHz, DMSO-d$_6$ + drop TFA-d): δ = 5.57(s, 2H), 7.20(dd, 1H), 7.40–7.55(m, 3H), 7.71(s, 1H), 7.79(d, 2H), 8.08 (d, 2H), 8.54(d, 1H), 8.91(d, 2H).<br><br>Analysis: Found: C, 61.22; H, 3.67; N, 3.33.<br>C$_{21}$H$_{15}$NO$_4$S$_2$; Requires: C, 61.59; H, 3.69; N, 3.42. |
| 82 | 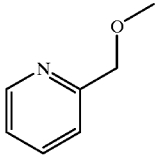 | m.p. 132–134° C.<br>LRMS(Thermospray): 366.3(MH$^+$-CO$_2$).<br>$^1$H NMR(300 MHz, DMSO-d$_6$): δ = 5.22(s, 2H), 7.15(dd, 1H), 7.32(m, 1H), 7.42–7.57(m, 4H), 7.70–7.86(m, 4H), 8.47(d, 1H), 8.56(d, 1H).<br>C$_{21}$H$_{15}$NO$_4$S$_2$ |
| 83 | 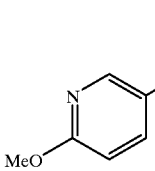 | m.p. 189–191° C.<br>LRMS(Thermospray): 440.0(MH+), 396.1(MH$^+$-CO$_2$).<br>$^1$H NMR(300 MHz, DMSO-d$_6$): δ = 3.85(s, 3H), 5.08(s, 2H), 6.82(d, 1H), 7.10(d, 1H), 7.43–7.58(m, 3H), 7.73–7.85(m, 4H), 8.28(s, 1H), 8.48(d, 1H).<br>C$_{22}$H$_{17}$NO$_5$S$_2$ |
| 85 | 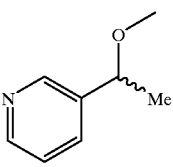 | mixture of diastereoisomers<br>LRMS(Thermospray): 380.1(MH$^+$-CO$_2$), 424.0(MH$^+$).<br>$^1$H NMR(300 MHz, DMSO-d$_6$): δ = 1.60(pair of d, 3H), 5.68(q, 1H), 7.09(dd, 1H), 7.35(m, 1H), 7.40–7.57(m, 3H), 7.63(m, 1H), 7.70–7.82(m, 3H), 8.40–8.50(m, 2H), 8.66(s, 1H).<br>C$_{22}$H$_{17}$NO$_4$S$_2$ |
| 86 | 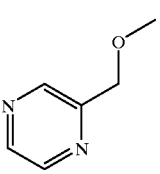 | m.p. 135–136° C.<br>LRMS(Thermospray): 366.7(MH$^+$-CO$_2$).<br>$^1$H NMR(400 MHz, DMSO-d$_6$): δ = 5.28(s, 2H), 7.14(d, 1H), 7.40–7.53(m, 3H), 7.72–7.79(m, 3H), 8.43(d, 1H), 8.59(s, 1H), 8.61(s, 1H), 8.78(s, 1H).<br>C$_{20}$H$_{14}$N$_2$O$_4$S$_2$ |
| 87 | 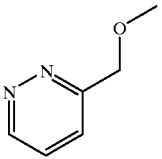 | m.p. 237–238° C.<br>LRMS(Thermospray): 367.6(MH$^+$-CO$_2$).<br>$^1$H NMR(400 MHz, DMSO-d$_6$): δ = 5.42(s, 2H), 7.13(d, 1H), 7.40–7.53(m, 3H), 7.65–7.80(m, 5H), 8.44(d, 1H), 9.17(d, 1H).<br>C$_{20}$H$_{14}$N$_2$O$_4$S$_2$ |

TABLE 13-continued

[Structure: benzothiophene with 3-(phenylsulfinyl), 2-CO₂H, and 6-O-CH₂-R² (where Y = O)]

| Example No | Y–R² (Y / R²) | Physical Data |
|---|---|---|
| 87 | pyrimidin-5-ylmethyl-O– | m.p. 251–252° C.<br>LRMS(APCI): 367.3(MH⁺-CO₂).<br>¹H NMR(400 MHz, DMSO-d₆): δ = 5.19(s, 2H), 7.18(dd, 1H), 7.40–7.52(m, 3H), 7.70–7.80(m, 3H), 8.43(d, 1H), 8.88(s, 2H), 9.13(s, 1H).<br>C₂₀H₁₄N₂O₄S₂ |
| 88 | pyridazin-4-ylmethyl-O– | 237–239° C.<br>LRMS(Thermospray): 367.1(MH⁺-CO₂).<br>¹H NMR(400 MHz, DMSO-d₆): δ = 5.29(s, 2H), 7.18(d, 1H), 7.42–7.55(m, 3H), 7.64–7.80(m, 4H), 8.50(d, 1H), 9.20(d, 1H), 9.28(s, 1H).<br>C₂₀H₁₄N₂O₄S₂ |
| 89 | 3-fluorobenzyl-O– | m.p. 206–208° C.<br>LRMS(Thermospray): 383.1(MH⁺-CO₂), 427.1(MH⁺).<br>¹H NMR(300 MHz, DMSO-d₆): δ = 5.18(s, 2H), 7.12(m, 2H), 7.27(d, 2H), 7.39–7.57(m, 4H), 7.75(s, 1H), 7.80(d, 2H), 8.49(d, 1H), 14.3(brs, 1H).<br><br>Analysis:  Found:  C, 61.64; H, 3.46.<br>C₂₂H₁₅FO₄S₂;  Requires:  C, 61.96; H, 3.55. |
| 90 | (1,3-benzodioxol-5-yl)methyl-O– | m.p. 185–186° C.<br>LRMS(Thermospray): 409.3(MH⁺-CO₂), 452.8(MH⁺).<br>¹H NMR(400 MHz, DMSO-d₆): δ = 5.01(s, 2H), 5.98(s, 2H), 6.85–6.95(m, 2H), 6.99(s, 1H), 7.05(d, 1H), 7.40–7.55(m, 3H), 7.68(s, 1H), 7.80(d, 2H), 8.43(d, 1H).<br>C₂₃H₁₆O₆S₂ |
| 91 | 3-cyanobenzyl-O– | m.p. 230–232° C.<br>¹H NMR(300 MHz, DMSO-d₆): δ = 5.20(s, 2H), 7.13(d, 1H), 7.43–7.62(m, 4H), 7.72–7.82(m, 5H), 7.93(s, 1H), 8.50(d, 1H).<br><br>Analysis:  Found:  C, 63.58; H, 3.66; N, 3.05.<br>C₂₃H₁₅NO₄S₂;  Requires:  C, 63.72; H, 3.49. N, 3.23 |
| 92 | thien-3-ylmethyl-O– | m.p. 110° C.<br>LRMS(Thermospray): 371.1(MH⁺-CO₂).<br>¹H NMR(300 MHz, DMSO-d₆): δ = 5.15(s, 2H), 7.08(d, 1H), 7.16(d, 1H), 7.43–7.60(m, 5H), 7.72–7.85(m, 3H), 8.46(d, 1H).<br>C₂₀H₁₄O₄S₃. |

TABLE 13-continued

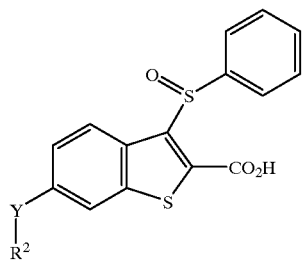

| Example N° | Y<br>/<br>R² | Physical Data |
|---|---|---|
| 93 |  | m.p. 244° C.<br>LRMS(Thermospray): 372.3(MH⁺-CO₂), 416.8(MH⁺).<br>¹H NMR(400 MHz, DMSO-d₆): δ = 5.44(s, 2H), 7.10(dd, 1H), 7.43–7.57(m, 3H), 7.76–7.83(m, 3H), 8.02(s, 1H), 8.49(d, 1H), 9.10(s, 1H).<br>C₁₉H₁₃NO₄S₃. |

Example 94

6-(1H-Imidazo[4,5-c]pyridin-1-ylmethyl)-3-[(3-methoxyphenyl)sulfinyl]benzo[b]thiophene-2-carboxylic Acid

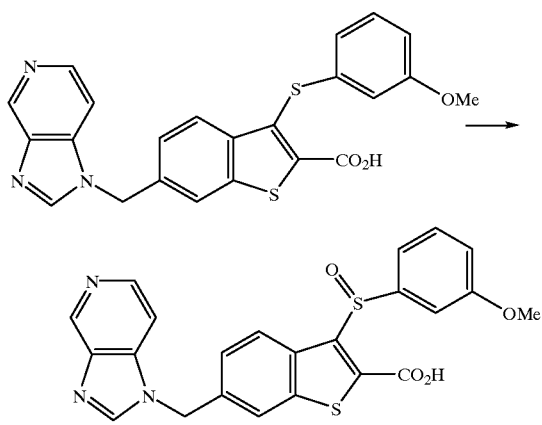

Hydrogen peroxide in water (0.07 ml of 30% w/v, 0.58 mmol) was added to a mixture of 6-(1H-Imidazo[4,5-c]pyridin-1-ylmethyl)-3-[(3-methoxyphenyl)sulfanyl]benzo[b]thiophene-2-carboxylic acid (Example 23—218 mg, 0.49 mmol) in acetic acid (2 ml), and 2M hydrochloric acid (2 ml). The solution was heated to 100° C. for 1 hour. The solution was cooled and the solvents were evaporated under reduced pressure. The residue was dissolved in a hot mixture of aqueous sodium hydroxide (5 ml of 1M) and methanol (5 ml). After acidifying the solution with acetic acid, and cooling, the precipitate was collected by filtration to give the title compound as a colourless solid (95 mg).

LRMS (Thermospray): 420.2 (MH⁺ —CO₂)

¹H NMR (300 MHz, DMSO-d₆): δ=3.73 (s, 3H), 5.65 (s, 2H), 6.98 (d, 1H), 7.30–7.45 (m, 4H), 7.71 (d, 1H), 8.01 (s, 1H), 8.36 (d, 1H), 8.53 (d, 1H), 8.64 (s, 1H), 9.05 (s, 1H).
C₂₃H₁₇N₃O₄S₂

Example 95 & 96

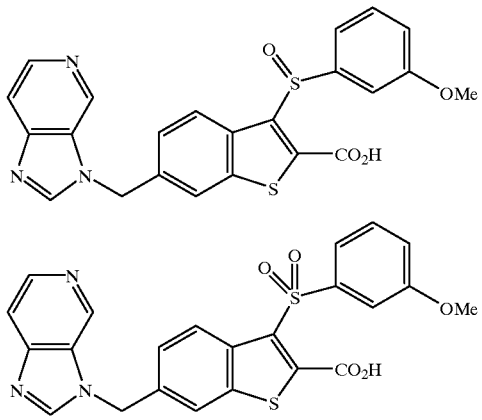

6-(3H-Imidazo[4,5-c]pyridin-3-ylmethyl)-3-[(3-methoxyphenyl)sulfinyl]benzo[b]thiophene-2-carboxylate

&

6-(3H-Imidazo[4,5-c]pyridin-3-ylmethyl)-3-[(3-methoxyphenyl)sulfonyl]benzo[b]thiophene-2-carboxylate The title compounds were prepared from the compound of Example 22 using the method of Example 94, as a colourless solid comprising a 1:1 mixture of sulfinyl (Example 95) and sulfonyl (Example 96) analogues.

LRMS (APCI): 419.9 (sulfinyl M⁺ —CO₂), 436.2 (sulfonyl M⁺ —CO₂) C₂₃H₁₇N₃O₄S₂ & C₂₃H₁₇N₃O₅S₂

Example 97

3-[2-(Methylsulfonylamino)phenyl]sulfanyl-6-(3-pyridylmethoxy)benzo[b]thiophene-2-carboxylic Acid

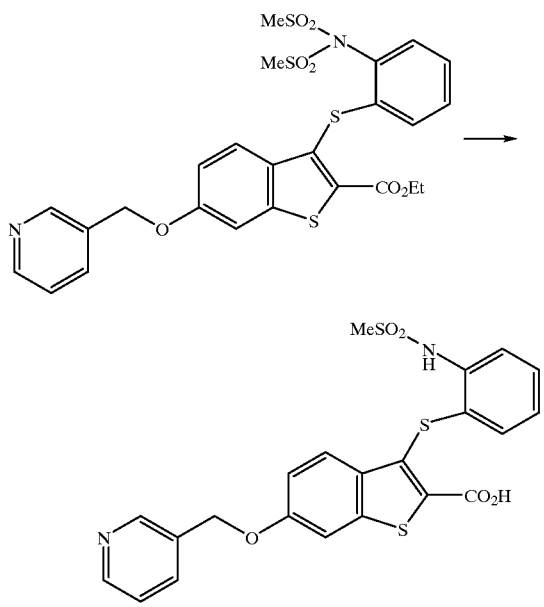

Sodium hydroxide (1 ml of 1M in water) was added to a solution of ethyl 3-[2-(N,N-dimethylsulfonylamino)phenyl]sulfanyl-6-(3-pyridylmethoxy)benzo[b]thiophene-2-carboxylate (Example 16—185 mg, 0.31 mmol) in methanol (5 ml), and the solution was heated at reflux for 40 minutes. The hot solution was acidified by dropwise addition of acetic acid, diluted with water (5 ml), and cooled. The solid precipitate was isolated by filtration and dried under vacuo to give the title compound as a colourless solid (102 mg).

m.p. 258–260° C.

LRMS (Thermospray): 487.4 (MH$^+$), 442.8 (MH$^+$ —CO$_2$).

$^1$H NMR (300 MHz, DMSO-d$_6$): δ=3.08 (s, 3H), 5.20 (s, 2H), 6.72 (d, 1H), 6.99–7.13 (m, 2H), 7.18 (t, 1H), 7.35 (d, 1H), 7.40 (dd, 1H), 7.59 (d, 1H), 7.78 (s, 1H), 7.87 (d, 1H), 8.54 (d, 1H), 8.67 (s, 1H), 9.48 (s, 1H), 13.60 (brs, 1H).

Analysis: Found: C, 53.81; H, 3.73; N, 5.58. C$_{22}$H$_{18}$N$_2$O$_5$S$_3$ Requires: C, 54.30; H, 3.73; N, 5.76.

Example 98

3-[2-(Hydroxymethyl)phenylsulfinyl]-6-(3-pyridylmethoxy)benzo[b]thiophene-2-carboxylic Acid

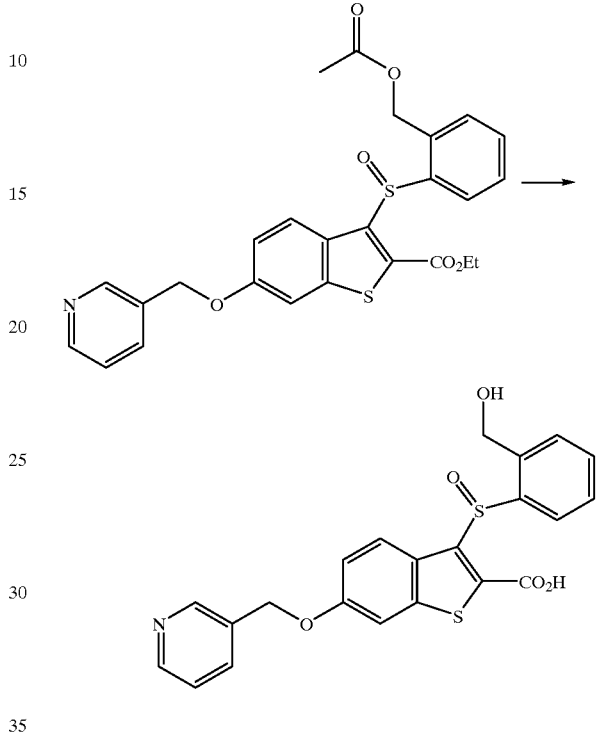

Sodium hydroxide (3 ml of 1M in water) was added to a suspension of ethyl 3-(2-[(methylcarbonyloxy)methyl]phenylsulfinyl)-6-(3-pyridylmethoxy)benzo[b]thiophene-2-carboxylate (Example 35—500 mg, 0.98 mmol) in methanol (15 ml). The mixture was heated to reflux for 30 minutes. The resultant solution was cooled, diluted with water and acidified by dropwise addition of acetic acid. The precipitate was isolated by filtration and washing with water. The solid was recrystallised twice by dissolving in hot methanol, and cooling, to give the title compound as a colourless solid (71 mg).

m.p. 210° C.

LRMS (Thermospray): 395.7 (MH$^+$ —CO$_2$).

$^1$H NMR (400 MHz, DMSO-d$_6$): δ=[4.42 (d, 1H) & 4.78 (d, 1H) non-equivalent CH$_2$OH], 5.21 (s, 2H), 5.40 (brs, 1H), 7.13 (d, 1H), 7.40–7.60 (m, 4H), 7.77–7.82 (m, 2H), 7.90 (d, 1H), 8.44 (d, 1H), 8.56 (d, 1H), 8.70 (s, 1H). C$_{22}$H$_{17}$NO$_5$S$_2$

Example 99

The compounds of Examples 56 and 71 were tested in Test B above using rat aorta, and found to have pA$_2$ values of 7.83 and 6.64 respectively.

We claim:
1. A compound of formula I,

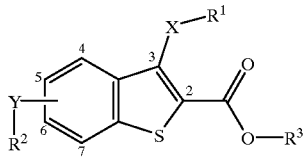

wherein
X represents O or S(O)$_m$;
R$^1$ and R$^2$ independently represent phenyl, naphthyl or heteroaryl containing 1, 2 or 3 heteroatoms independently selected from N, S and O; the ring being optionally fused to a saturated or unsaturated heterocyclic ring containing 1, 2 or 3 heteroatoms independently selected from N, S and O; the ring system as a whole being optionally substituted by one or more groups selected from OH, halogen, CN, NH$_2$, (CH$_3$SO$_2$)HN, (CH$_3$SO)$_2$N, C$_{1-6}$ alkyl (optionally substituted by OH or CH$_3$CO$_2$) and C$_{1-6}$ alkoxy;
Y represents a bond, O, (CH$_2$)$_n$, O(CH$_2$)$_n$, (CH$_2$)$_n$O, or CH(C$_{1-6}$ alkyl)O;
R$^3$ represents H or C$_{1-6}$ alkyl;
m represents 0, 1, or 2; and
n represents 1, or 2;
provided that:
(i) when R$^2$ is linked to Y via a nitrogen atom, then Y does not represent O, O(CH$_2$)$_n$ or CH$_2$O; and
(ii) when R$^3$ represents H, then neither R$^1$ nor R$^2$ is substituted by (CH$_3$SO$_2$)$_2$N;

or a pharmaceutically acceptable salt thereof.

2. A compound as claimed in claim 1, wherein X represents SO or S.

3. A compound as claimed in claim 2, wherein R$^1$ represents phenyl or substituted phenyl.

4. A compound as claimed in claim 1 wherein R$^2$ represents 3-pyridyl, 5-pyrimidinyl, 1-imidazolyl, imidazo[4,5-c]pyridin-3-yl or 3-thienyl.

5. A compound as claimed in claim 1 wherein Y represents CH$_2$, CH$_2$O or OCH$_2$.

6. A compound as claimed in claim 1 wherein Y is attached to the 6-position of the benzothiophene ring.

7. A compound as claimed in claim 1 wherein R$^3$ represents H.

8. A compound as claimed in claim 1 wherein a heteroatom in R$^2$ is separated from the benzothiophene ring by 4 atoms.

9. A pharmaceutical formulation comprising a therapeutically effective amount of a compound of formula I, as defined in claim 1, or a pharmaceutically acceptable salt thereof, and a pharmaceutically acceptable adjuvant, diluent or carrier.

10. A method of treatment of restenosis, renal failure, pulmonary hypertension, benign prostatic hypertrophy, male erectile dysfunction, congestive heart failure, stroke, angina, atherosclerosis, cerebral and cardiac ischaemia or cyclosporin induced nephrotoxicity, which comprises administering a therapeutically effective amount of a compound of formula I, as defined in claim 1, or a pharmaceutically acceptable salt thereof, to a patient in need of such treatment.

* * * * *